United States Patent [19]
Margerum et al.

[11] Patent Number: 5,834,020
[45] Date of Patent: Nov. 10, 1998

[54] DENDRIMERIC COMPOUNDS

[75] Inventors: Larry Margerum, Wayne, Pa.; Brian Campion, Solano Beach, Calif.; Jere Douglas Fellmann, Livermore, Calif.; Martha Garrity, San Clemente, Calif.

[73] Assignee: Nycomed Salutar, Inc., Wayne, Pa.

[21] Appl. No.: 722,082

[22] PCT Filed: Apr. 20, 1995

[86] PCT No.: PCT/GB95/00898

§ 371 Date: Jan. 21, 1997

§ 102(e) Date: Jan. 21, 1997

[87] PCT Pub. No.: WO95/28966

PCT Pub. Date: Nov. 2, 1995

[30] Foreign Application Priority Data

Apr. 20, 1994 [GB] United Kingdom .................. 9407812

[51] Int. Cl.⁶ .................................................. A61K 9/00
[52] U.S. Cl. .................... 424/484; 424/485; 424/486; 424/DIG. 16; 424/1.11; 424/9.1
[58] Field of Search ................ 424/DIG. 16, 484–489, 424/1.11, 1.33, 1.37, 9.1

[56] References Cited

U.S. PATENT DOCUMENTS 5,157,095 10/1992 Smid ......................................... 528/15
5,338,532 8/1994 Tomalia et al. ......................... 424/1.49

FOREIGN PATENT DOCUMENTS

| 0 430 863 | 6/1991 | European Pat. Off. . |
| 3-263431 | 11/1991 | Japan . |
| 88/01178 | 2/1988 | WIPO . |
| 90/12050 | 10/1990 | WIPO . |
| 90/14881 | 12/1990 | WIPO . |
| 91/14460 | 10/1991 | WIPO . |
| 93/06868 | 4/1993 | WIPO . |

OTHER PUBLICATIONS

Gerhard et al., "Dynamic Contrast–Enhanced MR Imaging of the Upper Abdomen: Enhancement Properties of Gadobutrol, Gadolinium–DTPA–Polylysine . . . " *Magn. Reson. Med.*, 32(5):622–628 (1994).

Wiener et al., "Dendrimer–Bates Metal Chelates: A New Class of MRI Contrast Agents" *Magnetic Resonance in Medicine*, 31(1):1–8 (1994).

*Primary Examiner*—Neil S. Levy
*Attorney, Agent, or Firm*—Fish & Richardson P.C.

[57] ABSTRACT

The invention provides a dendrimeric compound comprising a dendrimeric bioactive moiety with linked thereto a plurality of diagnostically or therapeutically active moieties characterized in that the molecular skeleton of said compound contains at least one biodegradable cleavage site such that on cleavage thereof said active moieties are released in renally excretable form.

17 Claims, No Drawings

DENDRIMERIC COMPOUNDS

This application is a 371 of PCT/GB95/00898, filed Apr. 20, 1995 with priority as a PCT Great Britain # 9407812.8 filed Apr. 20, 1994.

This invention relates to novel therapeutically or diagnostically useful dendrimeric compounds and their applications in medicine, including the field of diagnostic imaging.

Chelants and their metal chelates have long found utility in therapeutic and diagnostic medicine, most notably in metal detoxification, therapeutic delivery of radioisotopes, and in particular in diagnostic imaging.

Medical imaging modalities, such as MRI, X-ray, gamma scintigraphy, and CT scanning, have become extremely important tools in the diagnosis and treatment of illnesses. Some imaging of internal parts relies on inherent attributes of those parts, such as bones, to be differentiated from surrounding tissue in a particular type of imaging, such as X-ray. Other organs and anatomical components are only visible when they are specifically highlighted by particular imaging techniques.

Researchers have recognized for many years that chelating various metals increases the physiologically tolerable dosage of such metals and so permits their use in vivo as contrast agents to enhance images of body parts (see for example C. D. Russell and A. G. Speiser, J. Nucl. Med. 21: 1086 (1988) and U.S. Pat. No. 4,647,447 (Gries et al.)). However, such simple metal chelate image enhancers, without further modification, do not generally provide any particularly significant site specificity.

In recent years many developments in the field of chelate-based contrast agents have taken place and new and more diverse chelants have been developed which enable specific application, eg. imaging of target organs, of blood flow, of axonal transport, etc. For example, the hepatobiliary system may be selectively imaged by MRI using lipophilic contrast agents, or the contrast agent may be targetted to a specific organ or area of the body by means of a target-specific biomolecule, such as an antibody, to which the chelant moiety is coupled.

More recently efforts have been directed to producing chelants, including target-specific site-directed chelants, which have a multiplicity of sites for metal chelation. This may be achieved by creating oligochelants, as described by Nycomed Salutar, Inc. in WO-91/05762, which have a linear or branched oligomeric structure comprising alternating chelant and linker moieties.

Alternatively, polychelant "magnifiers" may be formed which comprise a number of chelant moieties attached to a backbone or carrier structure, as described for example by Nycomed Salutar, Inc. in WO-90/12050 and by Torchlin et al. in Hybridoma, 6: 229–240 (1987). Such a backbone may comprise a simple chain-like polymer, eg. a polyamine or polypeptide, or a dendrimer (eg. a starburst dendrimer as described by Tomalia et al. in Polymer Journal 17: 117 (1985) and in U.S. Pat. No. 4,587,329). To produce a site-specific polychelant, one or more of such chelant moiety carrying backbone molecules may be conjugated to a site-directed macromolecule, eg. a protein.

Polychelants have the advantage that each molecule can be loaded with several metal ions, and thus metal ion delivery to the target site or area is increased, thereby enabling much more effective targeting of a therapeutic or diagnostic metal and achieving enhanced efficacy as a contrast agent. Also, in view of their increased size, soluble metal-containing polychelates have a unique localisation and biodistribution in the body which renders them particularly useful as so-called "blood-pool" contrast agents; by virtue of their non-particulate nature and relatively high molecular weights, such polychelants do not diffuse immediately into the extravascular space (as is the case with the monomeric chelates presently used in MRI contrast enhancement such as Gd DTPA-BMA and Gd DTPA) and remain circulating in the blood pool. This extended intravascular residence time means that the polychelates may function as target-specific blood pool agents without requiring attachment to a site-directed biomolecule.

However, although representing a considerable advance in the art, such polychelates are not entirely satisfactory. In particular, concerns have been raised that the polychelates may not undergo sufficiently rapid metabolism in vivo and may in some cases be recognised as small particles or protein-like material and thus be removed from the blood and into the liver. One potentially serious consequence of this, would be that the levels of polychelate in the body could build up to unacceptable toxic levels. Indeed, intracellular retention of synthetic polymers, particularly in liver cells, has been reported in the literature (see for example Biochim Biophys Acta 587: 282 (1979)).

There is therefore a continuing need for new and improved polychelant molecules. The present invention seeks to fulfil this need and in particular to provide improved magnifier-type polychelant molecules with desirable pharmacodynamics in terms of bioelimination.

We have now found that improved biodistribution and bioelimination can be achieved by formation of dendrimer-based molecules with built in biodegradation cleavage sites. The resultant structures, useful as diagnostic or therapeutic agents according to the choice of active entity loaded onto the dendrimer frames, can be designed to achieve desired distribution and elimination targets.

Thus, in one aspect the present invention provides a dendrimer compound comprising a dendrimeric backbone moiety with linked thereto a plurality of diagnostically or therapeutically active moieties (e.g. chelant moieties capable of complexing metal ions), characterised in that the molecular skeleton of the compound contains at least one biodegradation cleavage site such that on cleavage thereof said active moieties are released in renally excretable form, and preferably such that the dendrimeric backbone or the fragments thereof is also released in renally excretable form.

In the compounds of the invention, the biodegradation sites may be remote from the dendrimeric backbone moiety, but in preferred embodiments the backbone incorporates such sites, especially at branching positions.

A dendrimeric (or cascade) polymer, such as that forming the backbone moiety in the compounds of the invention, is formed using a core monomer, the zero generation dendrimer, having at least two, preferably 2 to 20, especially 3 to 12, polymerization sites, to which are coupled monomers having at least three polymerization sites and as a result acting as branching sites. With each successive branching a new "generation" dendrimer is formed. Thus, a dendrimer is typically a polymer having a polyvalent core that is covalently bonded to at least two dendritic "branches".

For the compounds of the invention, zero to eighth, particularly third to sixth, generation dendrimer structures are preferred. Where the structure carries a biodistribution modifier as described below such as PEG, fourth generation is preferred while without such modifiers fourth and fifth generation are particularly preferred.

Biodegradability for the dendrimeric backbone may be achieved by incorporating biodegradable bonds into the dendrimeric structure, e.g. at branching sites or in the dendrimer arms. These bonds may be in organic or inorganic functions although in a preferred embodiment of the invention at least one branching site of the dendrimeric backbone is biodegradable and comprises a polyatomic structure containing at least one heteroatom in its backbone structure. Such biodegradable branching sites will be referred to herein as inorganic biodegradable sites or structures.

Preferably such biodegradation sites will be towards the core of the dendrimer, eg. at a low generation branching site or branch such as the first, second, third, etc. generation branching sites or branches.

In this way biodegradation of the dendrimer results in fragmentation of the dendrimeric backbone, e.g. to produce fragments which can be excreted renally. Preferably the biodegradation site or sites are so positioned within the dendrimeric structure as to produce relatively uniform fragments on breakdown.

In one simple embodiment, the compounds may have a primary biodegradation site at the core of the dendrimer and in the discussion below biodegradable branching sites are referred to generally as dendrimer cores.

In another preferred embodiment however the dendrimeric compounds of the invention may have more than one biodegradable site, particularly preferably arranged such that a first biodegradable site (or set of sites) is located towards the periphery of the compound and a second site or set of sites is located at or further towards the core, and so on. In this way biodegradation can proceed in a step-wise fashion with the inner biodegradation sites becoming relatively more exposed (and hence liable to breakdown) as breakdown occurs at the outer degradation sites. Particularly preferably, in such compounds the outer degradation sites will be at or near the active moiety attachment sites so that, in vivo, low molecular weight rapidly eliminatable moieties are cleaved from the dendrimeric structure which itself can then break down further. For such compounds, the biodegradation sites may all be provided by biodegradable inorganic structures at branching sites, alternatively however the biodegradation sites may be provided by biodegradable organic structures, e.g. ester, carbamate, double ester or disulphide linker groups, attached directly or indirectly to branching sites or to the dendrimeric frame.

Double ester bonds, i.e. bonds of formula —O—CO—O—CH$_2$—O—CO—O— from which one or both of the terminal oxygens may be omitted and in which the methylene group may be substituted, are particularly suitable as biodegradable bonds.

Particularly preferably the compounds according to the invention will have a dendrimeric backbone moiety with attached thereto through biodegradable structures, particularly organic structures, a plurality of active moieties and optionally one or more biodistribution modifying moieties, e.g. polyhydroxyalkyl or hydroxypolyalkoxyalkyl groups.

This cleavable structure permits faster excretion of the therapeutically or diagnostically active moieties, e.g. biotolerable metal mono-, di- or oligochelates, whilst still retaining the advantages for production and administration of the monodisperse polymer system.

The compounds of the invention thus combine the advantages of well defined monodisperse dendrimer-based compounds with the advantages that follow from having the in-built facility to biodegrade to more readily eliminatable low molecular weight fragments, eg. dendrimer fragments and mono-, di- or oligochelant molecules.

The dendrimeric compounds of the invention and the derivatives (e.g. salts and chelates) thereof are here termed "magnifiers". The "active" groups carried by the dendrimeric frame may be any groups having desired diagnostic or therapeutic efficacy and the frame may also be used to carry groups (modifiers) which serve to modify the biodistribution of the compound, e.g. site-directed molecules which cause the compound to distribute to desired tissue or body sites, hydrophilic or lipophilic groups, or protein-binding inhibitors.

Suitable diagnostically active groups include chelant moieties, such that when the dendrimeric compound is metallated with appropriate paramagnetic metal, radioactive metal or heavy metal ions or with polyatomic ions it can serve for example as an MR, X-ray, EIT or scintigraphic contrast agent.

The chelant moieties in such magnifiers are capable of chelating metal ions with a high level of stability, and are metallated with the appropriate metal ion(s), e.g. to enhance images and/or to deliver cytotoxic doses of radioactivity.

Other diagnostically active moieties that may be loaded onto the dendrimeric frame include halogenated, especially fluorinated or iodinated, groups for example haloalkyl or haloaryl groups. The resulting dendrimeric compounds may then be suited for use as MR or X-ray contrast agents. Particularly suitable such groups include polyhalo $C_{1-6}$-alkyl and triodophenyl moieties. The MR and X-ray contrast agent literature contains many suggestions of halogenated organic groups or tungsten-containing chelates which provide efficient MR or X-ray contrast enhancement and may readily be loaded onto a dendrimeric frame (see for example Haavaldsen et al. Acta Pharm Suec 20:219 (1983) and Speck "X-ray contrast media" Springer Verlag, 1991.

Therapeutically active groups may be intended to exercise their therapeutic effect while attached to the dendrimeric frame, e.g. as may be the case with chelated metal radioisotopes, with biodegradation serving to allow their subsequent bioelimination. Alternatively the dendrimeric compound may serve as a pro-drug allowing, on degradation of the bonds binding the therapeutically active group to the frame, the prolonged controlled release of the drug in its active form. The loading of therapeutic groups onto the dendrimeric frame may be achieved by conventional chemical techniques. Thus for example antihypertensives and other bioactive agents such as prazosin, naltrexone, clonidine and trimazosin may be loaded via biodegradable carbamate or carbonate bonds using procedures analogous to those of Li et al. described in Chapter 11 of "Polymeric drugs and drug delivery systems", ACS 1991.

As mentioned above, if desired, the compounds of the invention may carry biodistribution modifying moieties, such as for example polyhydroxyalkyl groups which enhance solubility, and polyethylene glycol (PEG) residues which prolong blood residence time. Other biodistribution modifiers that can be used are site-directed molecules, e.g. proteins or protein fragments. These may be attached via biodegradable or non-biodegradable linkages as desired, by conventional techniques.

Attachment to a site-directed molecule creates bifunctional agents which can enhance images and/or deliver cytotoxic doses of radioactivity to the targeted cells, tissues, organs, and/or body ducts. Alternatively, diagnostically active magnifiers may be used as liver or blood pool agents without being coupled to site directed molecules.

For use as blood pool agents however, the magnifiers will preferably be coupled to protein-binding inhibiting moieties, i.e. biodistribution modifiers such as PEGs, peptides or carbohydrates (e.g. glycosaminoglycans) which prolong blood residence time by hindering the binding of the blood proteins which facilitate abstraction of the dendrimer from the blood by the reticuloendothelial system.

Besides PEGS, other alkylene oxide polymers (e.g. propylene oxide polymers) may of course be used as protein-binding inhibitors. Similarly polydextran and polysaccharides such as amylose, amylopectin, starch, glycogen and in particular heparin and other glycosaminoglycans such as chondroitin-4-sulphates, chondroitin-6-sulphate, keratan, dermatan and heparan may be used.

Preferably such modifiers will have molecular weights of up to 40 kD, especially preferably in the range 100 D to 30 kD, particularly 500 D to 20 kD, more especially below 10 kD.

Thus particularly preferred as compounds of the invention are those of formula I

$$D(L_1A)_n(L_2M)_m \qquad (I)$$

(where D is a dendrimeric backbone moiety, preferably incorporating a biodegradable inorganic structure, especially preferably a third to sixth generation, structure; each A is a diagnostically or therapeutically active moiety, e.g. a chelant moiety, especially preferably a macrocyclic chelant, or a chelate thereof; each M is a biodistribution modifier, especially preferably a protein-binding inhibitor or a water solubility enhancer; $L_1$ and $L_2$ are bonds or linker moieties, preferably biodegradable linker moieties; n is a positive integer, preferably 3 to 200; and m is zero or a positive integer, no larger than n).

The magnifier polychelates according to the invention are especially suited for use in enhancing images of selected mammalian organs, tissues, cells, and the like, in vivo, using Magnetic Resonance Imaging (MRI), X-ray, gamma scintigraphy, light imaging and CT scanning, by virtue of their enhanced imaging properties and site specificity. The magnifier polychelants are also well suited for metal detoxification, therapeutic delivery of radioisotopes or therapeutic metal ions or polyatomic ions and for diagnostic nuclear medicine applications.

The magnifiers are in and of themselves useful entities in medical diagnosis and therapy, due in part to their unique localization in the body. The shape, charge and size of the magnifier, typically 1 to 100 kD, especially 5 to 90 kD, more especially 20 to 90 kD, particularly 30 to 85 kD, eg 40 to 50 kD, radically alters its biodistribution. The magnifiers generally have extended intravascular residence times, generally of the order of hours (and usually will eventually clear into the extracellular fluid (ECF) space and undergo renal excretion). Thus as these magnifiers remain primarily in the intravascular system for a diagnostically useful residence time, they are suitable for a range of uses such as blood pool and cardiac perfusion imaging, cerebral imaging, blood vessel imaging, in the imaging of the lungs for the evaluation of pulmonary disease, CNS tumour detection, lymphography and volume determination and thrombus detection and angiography. As blood pool agents they are particularly suited to use in studies of blood flow or volume, especially in relation to lesion detection and myocardial perfusion studies. The conventional monomeric MRI contrast agents which rapidly disperse into the extracellular/extravascular space cannot readily be used for these purposes. Moreover in view of their enhanced relaxivity, the MRI contrast agents according to the invention can be administered at significantly reduced dosages relative to current monomeric MRI contrast agents such as GdDTPA and GdDOTA, thus providing a significantly improved safety margin in their use.

The invention also enables water-soluble MRI contrast agents to be produced which can safely be administered orally for efficient liver imaging. For such agents the dendrimeric polychelant would preferably be used as the vehicle for Mn (II), Fe (III), Gd (III) or Dy (III) paramagnetic ions for optimum MR efficiency.

Furthermore, by suitable selection of chelated species, chelates according to the invention may be produced which are capable of functioning as X-ray agents (for example by choosing tungsten or molybdenum or chelatable metal clusters such as tungsten's polyoxoanions and their full or partial sulphur analogs as described for example in WO-A-91/14460 and WO-A-92/17215) and also as both MR and X-ray contrast agents by choosing an appropriate lanthanide metal ion. Where metal clusters are to be chelated, the chelant moieties are particularly conveniently EDTA, DTPA or TTHA derivatives, eg. such molecules carrying on their carbon backbone a functional group suitable for allowing attachment to the dendrimeric polymer backbone (e.g. a group

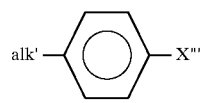

as described below). Such compounds may be prepared by known synthetic routes from paranitrobenzylglycine and polyaminoalkanes such as diethylenetriamine.

Attachment of the magnifier to a site-directed molecule results in even greater in vivo target specificity. The molecule is preferably an antibody, antibody fragment, other protein or other macromolecule which will travel in vivo to that site to deliver the diagnostically or therapeutically active entity. In the present invention the capacity of this site-directed macromolecule to travel and/or bind to its target is not compromised by the addition of the active entities, e.g. the chelated metals. For the polychelates, the number of chelates per molecule is sufficient to enhance the image of that particular target. These bifunctional polychelates are distinct entities, and desirably are substantially non-crosslinked.

In one preferred embodiment the magnifiers of the invention can be represented by the formula II

$$D(L_1Ch)_n \qquad (II)$$

where D is the residue of a dendrimeric backbone molecule, preferably one wherein the central core moiety is biodegradable and comprises a polyatomic structure containing at least one atom other than carbon in its backbone;
each Ch is independently the residue of a chelant (or a chelate or salt thereof);
n is an integer in the range of 3 to 200, preferably up to 100, eg 50 to 100;
and $L_1$ is a bond or a linker moiety, preferably comprising a biodegradable functionality, e.g. an ester, amide, disulphide, carbamate or double ester group.

Using this formula for the magnifiers, the corresponding bifunctional polychelants and polychelates of the invention can be represented by formula III

$$T\,(L_2D(L_1Ch)_n)_p \qquad (III)$$

where T is the residue of a site-directed molecule, each $D(L_1Ch)_n$ is independently the residue of a magnifier of formula II, $L_2$ is a bond or a linker moiety (as described for $L_1$ in formula II) which serves to link the magnifier to the site-directed molecule, and p is a positive integer, e.g. 1 to 10, preferably 1,2,3,4 or 5.

Likewise the corresponding blood pool magnifiers of the invention can be represented by formula IV $$(QL_2)_m D (L_1Ch)_n \qquad (IV)$$

(where $L_2$, m, D, Li, Ch and n are as defined above, m is a positive integer (e.g. 1 to 100, preferably 2 to 50) which is no larger than n, and each Q is a protein-binding inhibitor).

In such compounds biodegradable amide bonds will generally be polyamide functions subject to proteolysis mediated by endogenous proteases; single amide functions will not normally qualify as biodegradable.

The dendrimeric backbone molecule to which the active moieties are bound preferably has a multiplicity of attachment sites arranged to extend radially outwards from a central core moiety, i.e. a starburst dendrimer-type backbone molecule. Such starburst dendrimer-type backbone molecules comprise a central core moiety to which a plurality of linker groups are attached. These linker groups are terminally branched by the addition of further linking moieties which may each be the same or different to the first linker groups. A backbone molecule wherein a core group carries linker groups terminating with branching sites is the zeroth generation ($G_{0.0}$) dendrimer backbone molecule. Such a molecule which has itself been terminally branched once and again carries linker groups terminating with branching sites is termed a first-generation ($G_{1.0}$) backbone molecule. Generally the linker groups may be produced by condensation of two separate linker molecules, the second of which terminates with the branching sites and thus the zeroth generation dendrimer once terminally branched by first such linker molecules would be termed a 0.5 generation ($G_{0.5}$) dendrimer and the addition of the second linker molecules would produce the 1st generation ($G_{1.0}$) dendrimer having branching sites at the termini of the dendrimeric arms. Further terminal branching with such first and second linker molecules produces $G_{1.5}$, $G_{2.0}$, $G_{2.5}$ etc. dendrimers. With each successive round of branching, the number of attachment points available for bonding the active and modifier groups increases. In such a manner a starburst-type of dendrimer, analogous to the PAMAM starburst dendrimers of Tomalia (see Angew. Chem. 29:138 (1990) and Macromol. 19:2466 (1986)), may be formed.

According to a preferred embodiment of this invention, the core moiety of such a dendrimeric backbone may be any biodegradable polyatomic inorganic or partly inorganic structure (i.e. a structure having heteroatoms in its backbone) to which a multiplicity of groups (i.e. at least two but preferably at least three and especially preferably up to 20) may be attached. These groups may be linkers, or alternatively active or modifier groups. Thus while the dendrimer backbone in the magnifier of the invention is preferably at least second generation, it may be first or even zeroth generation. Where the dendrimer backbone is zeroth or first generation it may be desirable to use a biodegradable core comprising a cyclic moiety or a non-cyclic phosphorus-based moiety such as those discussed further below or alternatively or in addition it may be desirable to load the dendrimeric frame with polyfunctional active or modifier groups, e.g. oligochelants such as polylysinepolyDOTA.

By "biodegradable" is meant that the core (or other sites if the biodegradable moieties are sited elsewhere) is susceptible under physiological conditions to hydrolysis or other decomposition pathways thus causing the compound of the invention to be broken down into lower molecular weight parts which can either be eliminated without further transformation or can be otherwise metabolised in vivo much more readily than a comparable dendrimeric compound without the biodegradable branching site. In general, biodegradation will involve enzymic hydrolysis of particular chemical bonds in the dendrimeric compound, e.g. ester, urethane or polyamide groups, which are otherwise stable in the absence of enzymes. In other words, the overall structure is purposefully designed to fragment, preferably according to a well-defined mechanism, under physiological conditions in the body.

Preferably, the design of the compound is such that biodegradable bonds break to release the active moieties as identical lower molecular weight products. This has considerable advantages in terms of safety and identification.

It will be appreciated from the above discussion that this release of the active moieties may simply involve cleavage of a bond attaching the moiety to the dendrimeric frame liberating a monofunctional active moiety (e.g. a monochelate) or a polyfunctional moiety (e.g. an oligochelate) where the active moities are loaded in polyfunctional forms. Alternatively it may involve cleavage of a bond within the dendrimeric frame such that the active moiety is released attached to a fragment of the dendrimer. In either event if there is a dendrimer fragment remaining which is free of active groups, this too may be designed to biodegrade further, e.g. by inclusion of inorganic biodegradable branching sites or biodegradable bonds in the dendrimer arms, if it is otherwise too large for renal excretion. Once again however it is particularly desirable that the biodegradation products of any one kind (e.g. dendrimer framework fragments) should be uniform.

A preferred $G_0$ core moiety can be expressed by the general formula V $$B^{\cdot}(L^o R^o)_n. \qquad (V)$$

where $B^{\cdot}$ is a branching site which contains an optionally substituted polyatomic structure comprising at least two non-carbon atoms in its skeleton, preferably atoms selected from inorganic atoms such as nitrogen, phosphorus, silicon, boron and oxygen, optionally in the form of a homo- or heterocyclic ring preferably having 5–8 ring atoms, and preferably comprising in its skeleton at least two biodegradable bonds to non-carbon atoms;

$L^o$ is a bond or a zero generation linking group, e.g. a $C_{1-10}$ alkylene chain optionally interrupted by nitrogen, oxygen or sulphur atoms and optionally substituted by oxo or $C_{1-4}$ alkyl groups;

$R^o$ is a functional group capable of undergoing an addition, replacement or more preferably a condensation reaction whereby to conjugate at least one first-generation linker group $L^1$ to $B^{\cdot}L^o$, e.g. an amine, hydroxyl or carboxyl group or a derivative thereof, e.g. an ester, amide carbamate or double ester; and $n^o$ is an integer having a value of at least 2, preferably 3 to 8, especially 3 to 6;

or where $B^{\cdot}$ is itself capable of undergoing an addition, replacement or more preferably a condensation reaction whereby to conjugate at least one linker groups $L^1$ directly thereto, $n_o$ may also be zero or 1.

As may be inferred from the discussion of dendrimer generation terminology above, linker groups $L^o$ and $L^1$ and any higher generation linker groups may each derive from two different linker molecules. Thus $L^o$ may comprise two groups $L^o{}_1$, and $L^o{}_2$, the first bound to $B^o$ and the second to $R^o$. The bond between such groups is conveniently an ester, amide, double ester, disulphide or carbamate bond in which case the overall group $L^o$ would comprise an alkylene chain interrupted by oxygen, phosphorus, silicon, boron, sulphur or nitrogen atoms and optionally substituted by oxo groups.

Using analogous terminology, an Xth generation, $G_x$, dendrimer backbone molecule would have the general formula VI $$B^o(L^o(L^1(L^2 \ldots (L^x R^x)_{nx} \ldots)_{n2})_{n1})_n. \qquad (VI)$$

where $R^x$ is a functional group capable of being conjugated to a chelant moiety, e.g. an amine or ester group. By way of illustration, for the PAMAM starburst dendrimers $n^o$ is 3, each of $n^1$, $n^2$, $n^3$ etc are 2, and $R^x$ is an amine group).

The linking groups $L^1$, $L^2$ etc. and their sub-components $L^1_1$, $L^1_2$ etc. may be any of the linking groups used in conventional dendrimers, eg. the PAMAM starburst dendrimers.

In such dendrimeric compounds, the outer structure (e.g. the dendrimeric branches) can protect the biodegradable portions long enough for the dendrimeric compound to fulfill its desired function, eg. as a diagnostic imaging agent for blood pool imaging, before the compound is fragmented into lower molecular weight pieces. Some percentage of the material may pass through the kidney unchanged. Some may be degraded in the blood or kidney to create lower molecular weight materials which also pass through the kidney filtration system. However it is thought that the RES will deposit some percentage of the dendrimeric compounds into the liver, spleen and other RES organs. This process is thought to lead to intercellular retention of the dendrimer materials of this invention, lower molecular weight fragments are formed quickly and can exit the cell by active or passive transport mechanisms. Once out of the cell, the lower molecular weight fragments can exit the body by several pathways. For instance, the fragment can be secreted into the bile for processing into the feces. The fragment may also be reabsorbed into the bloodstream from the liver. Because it is now a lower molecular weight fragment, the compound can be filtered through the kidneys and into the urine.

The dendrimeric construction lends the advantage that the size and molecular weight of the polymer backbone can be controlled, and the undesirable non-specific cross-linking effects often observed with prior art-type linear backbone constructions (eg. those of Torchlin and Manabe, Supra) can be avoided.

One advantage of an inorganic-based core, in addition to the fact that it enables a biodegradable design to be achieved, is that it permits simplified characterisation by unique spectroscopic techniques, including nmr (especially $^{31}P$, $^{29}Si$, $^{11}B$). Dendrimer structure and growth from a symmetric core can easily be verified since the nmr spectrum is affected by changes in symmetry. Phosphate cores have the further advantage that the breakdown product of the core itself is highly biotolerable.

Furthermore, by using core structures having more branching sites than the ammonia cores of the PAMAM dendrimers it is possible to generate a dendrimeric backbone with the desired number of active moiety attachment sites within fewer synthetic stages.

Moreover, the core geometry may be designed to lead to larger or less dense dendrimers for a given generation as compared with the ammonia cores of the conventional starburst dendrimers described by Tomalia (supra). This can be achieved for example by adopting cyclic and $OPE_3$-based core structures as described below (E is oxygen or nitrogen).

Thus, dendrimeric compounds based on the novel core moieties according to the invention may exhibit blood retention (which is determined primarily by size) at lower molecular weights, thereby saving material.

A less dense structure may also have the advantage of better access for water (leading to lower viscosity, enhanced solubility, biodegradation and, for paramagnetic chelates, better relaxivity at the metal chelate sites) and for endogenous catabolic enzymes (to promote biodegration). Moreover, because of their polychelant nature, appropriate imaging doses of the compounds of the invention can be achieved at low osmolality. If desired a more open structure can be created by altering or substituting the groups at the attachment or branching sites, eg. so as to control the rate of degradation, eg. as a result of water or enzyme penetration. This may be done for example by incorporating a peptide or other spacer moiety in the linker groups to lengthen such groups, or by blocking one or more of the branching sites of the $R^o$, $R^1$ etc. groups to limit the degree of dendrimeric branching at one or more generation's branching sites.

The biodegradable cores in the magnifiers of the invention are conveniently moieties of formula VII $$Y[XY]_q \tag{VII}$$

(where each Y is a boron, phosphorus, silicon or nitrogen atom, carrying where valence dictates or permits groups R or $[X'Y']_q$, and each X is a carbon, oxygen, nitrogen, sulphur or silicon group, carrying, where valence permits or dictates, groups R or $[Y'X']_q$, with the provisos that if an X is carbon the Y groups it is attached to are nitrogen, boron or silicon, that where an X is silicon the Y groups it is attached to are silicon, and that at least two X-Y bonds in which X is not carbon are present unless $Y[XY]_q$ is a $(CN)_3$ ring, or $Y[XY]_q$ is $P[E]_3$, $OP[E]_3$ or $SP[E]_3$ where E is oxygen or nitrogen, or two non-adjacent Y groups can together represent a single Y group thereby, together with the intervening X and Y groups, creating a 4 to 10 membered, preferably 6 membered ring;

q is an integer having a value of up to 3, eg as valence permits or dictates;

X' and Y' are as defined for X and Y respectively but cannot carry side chains $[Y'X']_q$ or $[X'Y']_q$;

each R which may be the same or different represents a bond, a hydrogen atom or an oxo group.

With linker and branching groups attached, these biodegradable cores thus correspond to molecules of formula VIII $$Y''[X''Y'']_q \tag{VIII}$$

wherein q is as defined above;

Y" and X" are groups Y and X as defined above but wherein each R group which is a bond attaches a group X" or Y" to a group $R^o$, a group -Z-alk($R^o$), or a group $R^T$; each $R^*$ independently represents a group reactable to attach a dendrimer growing linker moiety;

each Z independently is a bond, an oxygen or sulphur atom or a group $NR^T$;

each alk independently is an arylene group or a $C_{1-10}$ alkylene group optionally interupted or terminated by an arylene group, and optionally substituted by oxo or $C_{1-4}$ alkyl groups or at nitrogen atoms by $R^T$ groups and optionally interrupted by oxygen, nitrogen or sulphur atoms;

s is a positive integer, eg. 1 to 6, preferably 1, 2 or 3; and each $R^T$ independently is a capping group, eg. an indolyl group or a $C_{1-6}$ alkyl group.

Examples of suitable alk groups include alkylene groups interrupted by peptide bonds and polypeptide chains as such or inserted within an alkylene chain.

Particularly preferably the compounds of formula V contain 2 to 20, especially 3 to 12 sites for attachment of dendrimer growing linker moieties. Also preferably they contain a total of 1 to 10, especially 6, X and Y groups.

Examples of particularly preferred XY backbones include the $(SiC)_3$, $(Si)_4$, $(SiO)_3$, $(Si)_5$, $(Si)_6$, $(Si)_7$, $(PO)_3$, $(NC)_3$, $(PN)_3$ and $(BN)_3$ rings and the acyclic $O=PN_3$, $O=PO_3$, $S=PN_3$ and $SPO_3$ structures.

Exemplary core structures according to the invention include phosphorus-based cores, and in particular, cores based on phosphite, phosphate ester and amide and phosphazene moieties, substituted with groups $R^o$ to enable dendrimer growth or attachment to a chelant moiety.

Suitable core structures thus include phosphate esters and phosphites of formulae (a) and (b), the phosphazenes of formula (c) and the phosphate amides of formula (d)

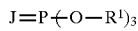  (a)

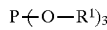  (b)

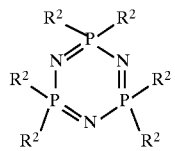  (c)

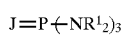  (d)

wherein J is O or S, and at least one of groups $R^1$ and $R^2$ is a group capable of reacting, eg. with primary amines or methacrylates, to continue dendrimer growth. Thus for example $R^1$ may be hydrogen, $R^T$ or -alk-$(R^{\cdot})_s$ (at least two $R^1$ groups in (a), (b) and (d) being other than $R^T$), and each $R^2$ may be a group $R^o$, $R^1$, $OR^1$, Hal, $-N=PHal_3$ or $-NR^1R^T$, (where Hal is a halogen atom, eg. chlorine) at least two $R^2$ groups being other than $R^T$;

s and alk are as defined above; and R is a reactive group as defined above, eg. providing a binding site for first generation linker molecules, eg. an amine, aldehyde, halogen, alkanesulphonyloxy or arylsulphonyloxy group, or an optionally esterified carboxyl group, eg. $COOR^3$ (where $R^3$ is a $C_{1-6}$ alkyl group)

In $R^2$ groups, any aryl moiety is preferably $C_6$ aryl, especially 1,4-phenylene, and any alkylene group is preferably linear $C_{1-6}$ alkylene.

Preferably, however in formulae (a), (b), (c) and (d) above all $R^1$ and $R^2$ groups are selected as defined above, to enable dendrimer growth leading to symmetrical substitution about the core.

Alternatively, to obtain different types of branching cores within the dendrimer selected $R^1$ and $R^2$ groups may be capping groups, e.g. imidazolyl groups, selected to terminate branching growth.

The use of imidazolyl capping groups is especially interesting due to the sensitivity to hydrolysis of such groups (see for example Allcock et al. Inorg Chem 21: 515 (1982)). Such groups thus offer the opportunity for greater control of the hydrolytic degradation of the dendrimeric polychelant.

Thus an exemplary phosphorus-based core may include a structure of formula (c')

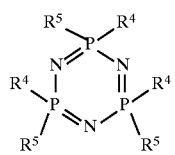  (c')

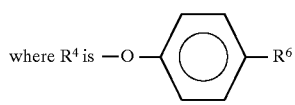

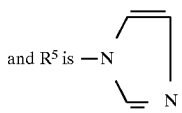

or $R^4$ and $R^5$ are independently selected from Hal and $-N=PHal_3$, $R^6$ is $COOCH_3$, $COOC_2H_5$ or $CH_2NH_2$ and $R^7$ is H or $-alk(R^o)_s$, eq. a structure of formula (c'')

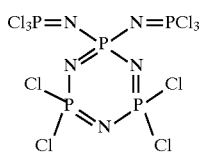  (c'')

(see for example Ngo et al., JACS 113: 5075 (1991)).

The advantage of such a molecule is that the rate of hydrolysis, and hence biodegradation could be controlled.

Phosphazenes are particularly advantageous in that they are multivalent; the ability of phosphazenes to have at least six branches stemming from the core phosphorus (as many as 12 from an amine phosphazene) results in the attainment of a higher number of terminal groups with fewer synthetic stages. The versatility of branching could also result in better control of water permeability through such polymers. This may improve relaxivity at metal centres and control rates of hydrolysis.

In addition, phosphazenes readily undergo hydrolysis into benign products such as ammonia and phosphates, which is important from the safety point of view (see Allcock references mentioned herein).

Phosphites, phosphate esters, phosphate amides and the phosphazene starting materials are well known, many are commercially available, and a well-developed synthetic methodology exists allowing flexibility for branching ie. attachment of monomer units. See for example Allcock et al Inorg. Chem. 21: 515 (1982) and in "Inorganic Polymers" Practice Hall, 1972. "Biodegradable Polymers" (1992), J. H. L. Crommen, E. H. Schacht, E. H. G. Mense, Bioomaterials, 13, 601. "Phosphorous-Nitrogen compounds", by H. R. Allcock, 1972, Academic Press. Allcock, et. al., IC. 1982, 21, 515.

Phosphites, phosphate esters, etc. and their synthesis are described for example in: "Phosphorus: An outline of its Chemistry" 4th Edition, D. E. C. Cororidge, Elsevier, 1990; Sokolowskii, J. Gen. Chem. USSR (Eng. Transl) 30: 3529 (1960); Dudek, Pr. Nauk, Inst. Technol. Nieorg. Nawozow Miner. Politech. Wroclaw 30: 3–9 (1986); Steinbach et al, Z. Anorg. Allg. Chem. 523: 180–186 (1985); Foss et al., Zh. Obshch. Khim. 48: 1713 (1978); U.S. Pat. Nos. 3,685,974; and 3,788,986.

Phosphazene synthesis is described in "Phosphazenes as Carrier Molecules for Bioactive Side Groups" ACS Monograph #232 (1983) H. R. Allcock; Cyclic phosphazene with six substitutions, JACS, 91: 3102, (1969); and (1970), 58. See also "Phosphorous-Nitrogen compounds", by H. R. Allcock, 1972, Academic Press.

Well characterised routes of core synthesis enable the size and hence the intravascular retention time of the resulting polychelates to be controlled.

Suitable synthesis strategies for phosphite and phophate ester cores include:

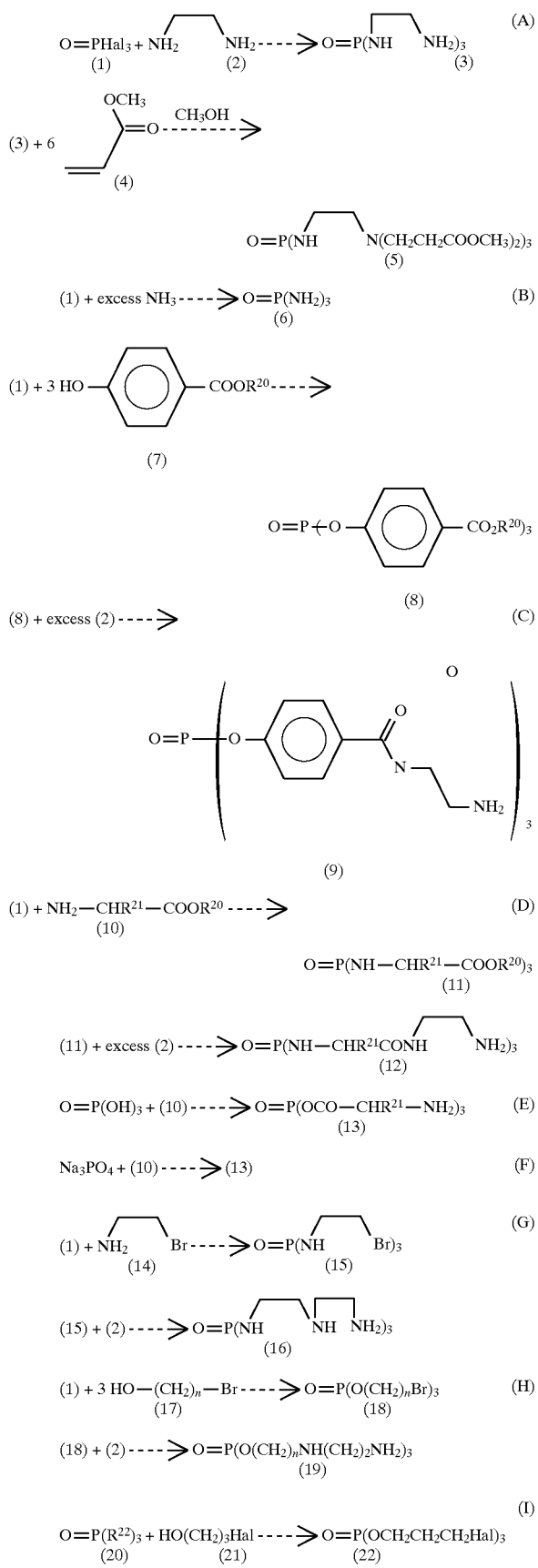

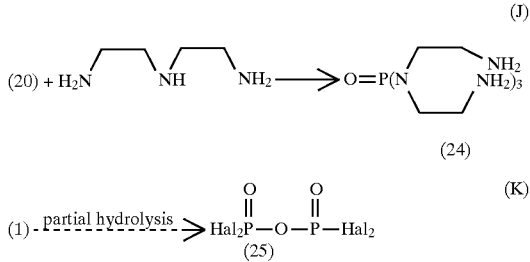

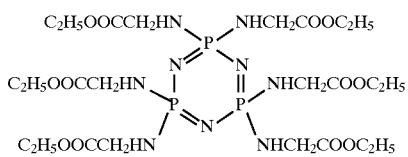

Compound (25), which is available from Aldrich, and PHal₃ can be used analogously to (1) in schemes such as those set down above. Pyrophosphoric acid ((HO)$_2$PO.O.PO (OH)$_2$) may also be used analogously and is available commercially.

In the above reaction schemes, Hal represents halogen, especially chlorine, $R^{20}$ is an alkyl group or another appropriate carboxyl blocking group, $R^{21}$ is hydrogen or an amino acid α-side chain, eg. an optionally aminated Cal alkyl group, $R^{22}$ is a $C_{1-6}$ alkyl group and the phosphite analogues of the starting materials may be used to produce compounds of formula (b).

In the schemes above, where condensation with an amino acid or derivative thereof is effected, this may be repeated to form a di- or oligo-peptide linkage which may thus have a tailored susceptibility to hydrolytic or enzymatic cleavage (see for example Crommen et al Biomaterials 13: 601 (1992) and Kopacek et al. Ann NY Acad Sci 446:93 (1985)). Moreover, by using amino acids such as lysine which have more than one amino function the opportunity for branching in the linker moiety is made available.

Other starting materials for OP(E)$_3$ cores (where E is nitrogen) include for example orthophosphoryl triamide OP(NH$_2$)$_3$ which can be made by the method of Goehring et al. Chem Ber. 89: 1771–1774 (1956).

Phosphazene cores may be prepared as described by Allcock et al. "Phosphazenes as carrier molecules for bio-active side groups" ACS monograph No. 233 (1983), JACS 91: 3102 (1969) and (1970) 58 and Inorg. Chem. 21: 515 (1982); thus the following compound may be prepared from hexachlorocyclotriphosphazene and ethyl glycinate:

A further advantage of phosphorus-based cores is, as mentioned above, ease of characterisation.

The sensitivity and natural abundance (100%) of spin active phosphorus ($^{31}$P) make it an ideal nucleus for characterisation. Geometric symmetry of the branching steps off of each P atom, would enable the immediate assessment of the synthetic success of the branching steps. There may also be an advantage, in vivo, to use of the unique $^{31}$P signal. Biodistribution and extent of metabolism may be measurable.

In addition the well known stretching frequencies P=N (1150–1400 cm$^{-1}$) P—O—Alkyl (ca 1040 cm$^{-1}$) and P—O—Aryl (ca 1220 cm$^{-1}$) could be useful in the analysis and characterisation of the molecule by IR spectroscopy. This is a significant advantage over the polyamine dendrimers of Tomalia (Supra) which have few spectroscopic handles.

Silicon-based cores form a further group of advantageous core moieties according to the invention. Such core structures may advantageously be based on silanes or siloxanes.

Polysiloxane starburst polymers are described by Morikawa et al. in Macromolecules, 24: 3469 (1991) and 25: 3247 (1992). Whilst the polymers described are unsuitable for use according to the invention, the siloxane monomer units may form the basis of cores according to the present invention, to which, for example polyamine linking groups ($L^1$, $L^2$ etc.) are attached to form eg. polyamine dendrimers.

Exemplary silicon based cores thus include cyclic and acyclic silanes and siloxanes

 (e)

where t is 0 or 1 and u is zero or a positive integer preferably 1 to 8; $R^7$ may represent a group $R^T$ or a group $R^*$ or Z-alk(-$R^*$)$_s$, at least two $R^7$ being R or Z-alk-($R^*$)$_s$, Z is a bond or an oxygen or sulphur atom or an imino group and alk($R^*$)$_s$ is as defined above, or two groups $R^7$ attached to different silicon atoms together represent a bond in a 5 to 8, preferably 6 or 7 membered ring, or a group $R^7$ represents a group of formula A

 (A)

wherein t and u are as defined above and $R^{7'}$ is as defined for $R^7$ but does not represent a group of formula A. In formula (e) above at least two Si—O or Si—N bonds must be present.

Thus examples of silicon-based cores of formula (e) include those of formula

where $R^{7'}$ is a group Z-alk($R^\circ$), as defined above, and v is 5, 6 or 7.

Such core species can readily be prepared using silicon chloride starting materials and indeed some such cyclic cores and precursors and analogues are already known (see West et al. Pure Appl. Chem. 54: 1041 (1982) and also Zhon et al J. Polymer Sci, Chem. Edit 29: 1097 (1991), and Polymer Preprints, 205th ACS Meeting, Denver Colo. 28.3.93 to 1.4.93, pages 822–823). Dendrimer growth from such cores is effected as discussed above for other core species.

Using silicon-chloride starting materials the core structures may be prepared for example according to the following schemes:

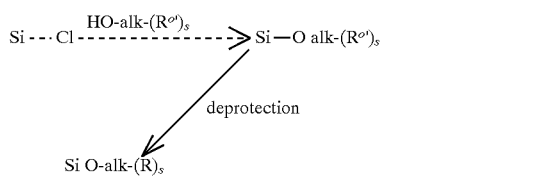

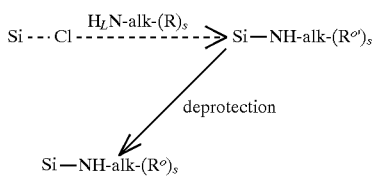

(where $R^{\prime\prime}$ is a protected $R^*$ group, eg. a Boc protected amine). Ester terminated -alk ($R^*$)$_s$ groups can if desired be produced by reaction of the silicon chloride with amino acid esters such as $NH_2CH_2COOEt.HCl$.

The advantage of such cores is that the degree of branching can readily be controlled. Also, the ability of silicon to undergo substitution via hypervalency, to produce unstable 5 or 6 coordinate intermediates is beneficial in enabling the preparation of dendrimers in which hydrolysis can be controlled, ie. to yield predictable fragments.

Silicon-based cores further have the advantage that they may be readily characterised by use of $^{29}$Si-nmr (eg. using polarization transfer pulse sequences such as DEPT and INEPT) and also IR and UV-VIS spectroscopy.

Boron-based cores form a further class of cores suitable for use according to the invention. Such a core may be based for example on a cyclic compound of formula (k)

$$[BR^{7'} \cdots X^2]_3$$ (k)

(where $R^{7'}$ is as defined above and $X^2$ is —O—, =N— or —$NR^{7'}$—) especially compounds of formulae (l) and (m)

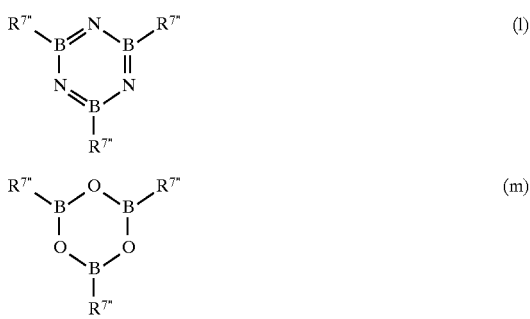

(where $R^{7''}$ is as defined above).

These too can be prepared by standard boron chemistry techniques analogous to the techniques described above eg. condensation of $R^{7'''} B(OH)_2$ (where $R^{7'''}$ is an optionally protected $R^{7'}$ group) or $BCl_3$ with ammonia followed by ring substitution.

Thus examples of synthetic routes to boron based cores include the following

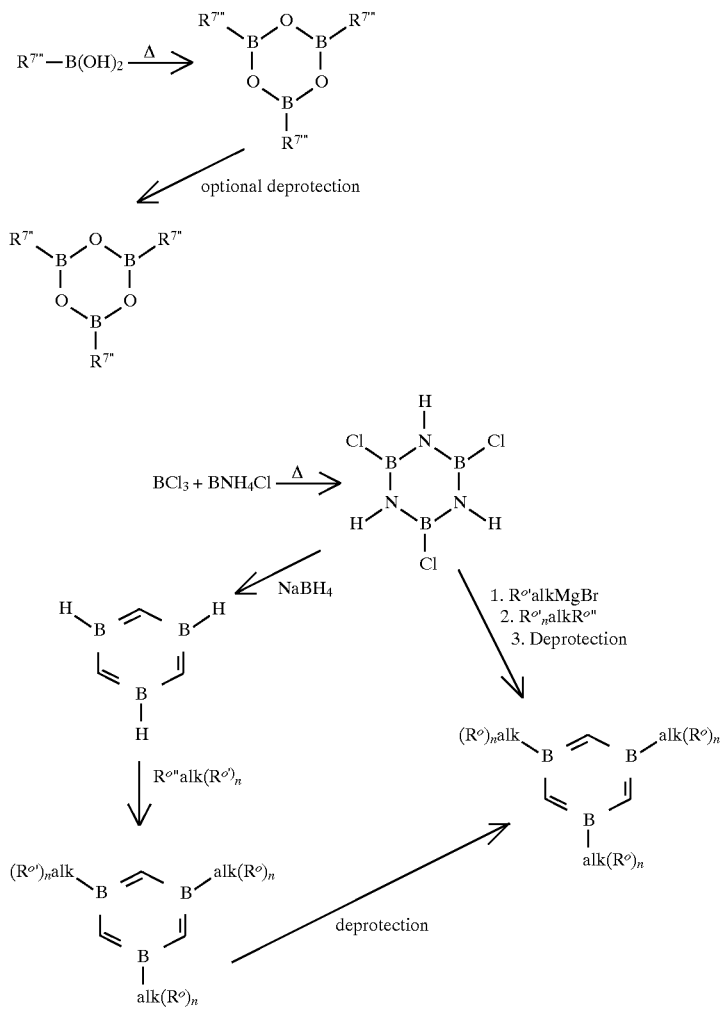

(where R" is a displaceable group (electrophilically or nucleophilically displaceable as appropriate), and $R^{7'''}$ is an optionally protected $R^{7'}$ group). Again terminal R groups may be modified, to replace terminal amines by the preferred terminal esters, and dendrimer production on such cores will be performed analogously to that on the other cores mentioned herein as well as the conventional dendrimer cores.

Boron-based cores have the advantages that they are readily degradable into benign metabolites such as $NH_4^+$ and $R—B(OH)_2$, that well defined and characterised synthetic strategies may be used to control synthesis and susceptibility to hydrolysis, and that nmr characterisation may be used.

A further significant advantage is that the presence of boron renders the dendrimers useful in neutron capture therapy.

Other cores which may be used include triazines of formula n

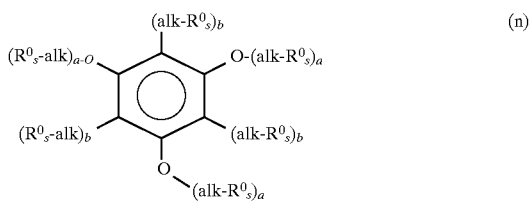

where R, alk and s are as described above and a and b are each 0 or 1 the sum of a and b being 1.

These triazines can be prepared for example from trialkyl triazines and triallyloxy triazines known from the literature or available from Aldrich in some cases, e.g.

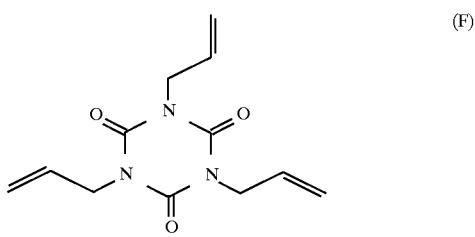

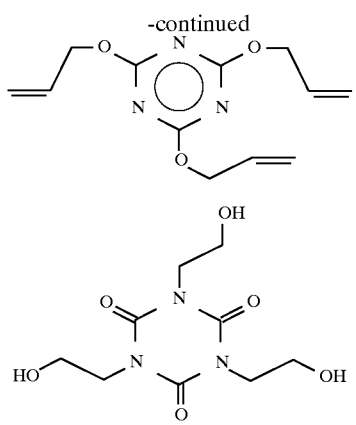

for example by reaction of (F) or (G) with Boc monoprotected ethylenediamine followed by deprotection or reaction of (H) with $SO_2Cl_2$ or another halogenating agent followed by reaction of the halide with ethylene diamine, etc.

Subsequent R group modification and dendrimer growth will again be carried out as discussed above.

In all cases, however the reaction conditions used for making and modifying the biodegradable, eg. hydrolytically sensitive, cores will of course be non-aqueous solvents such as methanol, toluene, acetonitrile, ethylenediamine, methylmethacrylate etc. Coupling reactions for dendrimer growth eg. with ethylenediamine or methylmethacrylate should be run at lower temperatures to avoid polymerization; in general ethylene diamine stages would be run at −5° to +10° C. while methylmethacrylate stages would be run at 20° to 40° C.

It will also be noted that while the preceding discussion has been concerned with biodegradable cores, such moieties may also, in alternative embodiments of the invention form one or more non-core branching sites in the dendrimeric structure. Equally the cyclic cores may have chelant or other active or modifier moieties attached directly to forming the zeroth generation dendrimeric compounds of the invention. Moreover, while the discussion above concentrates on biodegradable dendrimeric frameworks to which the active moieties may be attached, non-biodegradable dendrimeric frameworks, such as the PAMAM molecules of Tomalia (supra) may be used as described above to carry mono or polyfunctional active moieties bound via biodegradable linkages.

The linkage between the backbone D and the active (e.g. chelant) moiety A or the modifier M is thus optionally via biodegradable bond as described earlier. However in the case of chelant moieties these are preferably bound via an amide bond, the amide nitrogen deriving from the backbone molecule or more usually a linker moiety attached thereto and the amide carbonyl group deriving from a carboxyl or carboxyl derivative functionality on the chelant.

Thus in one embodiment the backbone (D): chelant (Ch) attachment may be represented as D—$L_3$—Ch (where $L_3$ is an optionally biocleavable linker moiety) and in another as D—$L_4$(Ch)$_s$ (where $L_4$ is an optionally biocleavable linker moiety and s is an integer greater than 1). In the latter case $L_4$ may be chosen such that it cleaves to release either mono or polychelates.

$L_3$ and $L_4$ preferably include one or more amino acids, to provide a hydrolysable spacer between dendrimer and chelant, e.g. one subject to protease mediated cleavage. Thus an amine terminating dendrimer can be linked to a chelant moiety AA—NH— $CH_2CH_2NHCOCH_2DO3A(Gd)$ where D03A(Gd) is a ring nitrogen attached, gadolinium-chelating, DO3A residue and AA is an oligoaminoacid spacer.

The magnifiers of the invention are produced by conjugating a plurality of active moieties onto a dendrimeric backbone molecule, generally a water-soluble polymer having reactive groups. The backbone dendrimer polymer will conveniently have at least 3 and preferably up to 400, particularly up to 384, especially up to 192, eg. up to 48, reactive groups. The reactive groups can be amines, preferably primary amines, carboxylates, esters, alcohols or thiolates etc.

Preferably the dendrimeric backbone polymers molecules are monodisperse, and if desired they may be radially symmetrical with each optionally branched linker group being identical.

One preferred group of chelating agents includes the macrocyclic agents having a 9 to 18 membered macrocyclic ring incorporating ring heteroatoms selected from O, N and S and having at least ring-attached side chain which optionally carry further metal coordinating groups or groups which alter the biodistribution of the chelate complex one of which side chains serves to link the macrocycle to the dendrimeric.

One preferred group of macrocyclic chelants can thus be represented by formula IX

 (IX)

where $X^3$ is O, S or $NR^{12}$ x is an integer having the value 3 to 8, preferably 3 or 4, w is an integer having the value 2 to 4, preferably 2 or 3, and $R^{12}$ is hydrogen or a side chain as referred to above, preferably a $C_{1-18}$alkyl group optionally substituted by a metal coordinating group, a chelating moiety, a hydrophilic group or a lipophilic group, linkage to such groups optionally being via an ester, amide, amine, alcohol or ether function.

Preferred macrocyclic skeletal moieties include the following polyazacycloalkanes:

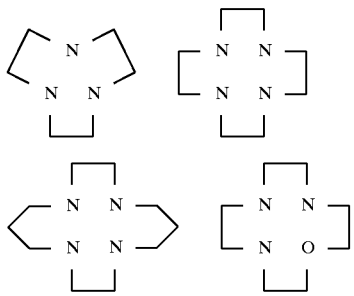

Non-hydrogen $R^{12}$ side chains are preferably attached at ring nitrogens although side chains linking to a hydrophilic or lipophilic group or to the dendrimer may conveniently be attached to a macrocyclic ring carbon.

Examples of coordinating groups which may be carried by the $R^{12}$ side chains, especially the ring nitrogen attached side chains, include COOH, $CONR_{22}^2$ (where $R^{22}$ is hydrogen or optionally substituted alkyl, ester amine or alcohol, eg. a $C_{1-6}$ alkyl group optionally substituted by amine, hydroxyl or $C_{1-4}$ alkoxy groups, for example a 2-aminoethyl group), CONHOH, $SO_3H$, $PO_3H$, hydroxy-phenyl, hydroxy-pyridyl, keto, and hydroxyl groups.

In this event, the coordinating group is preferably bound at the 1- or 2-positions of $R^{12}$, especially the 1-position. $R^{12}$ however is preferably not substituted at the 1-position by hydroxyl groups. Preferably the macrocyclic skeleton carries 2 to 4 and especially at least 3 such coordinating groups. Thus by way of example the chelating moiety may be a 1,4,7,10-tetraaza-1,4,7-triscarboxymethyl-10-(1,4-diaza-5-oxo-hexyl) cyclododecane.

Preferred hydrophilic $R^{12}$ groups include hydroxylated and/or alkoxylated alkyl groups such as 2-hydroxyethyl, 2-hydroxypropyl, 3-hydroxypropyl, 2,3-dihydroxypropyl, 2-hydroxy-butyl, 3-hydroxybutyl, 4-hydroxybutyl, 2,3-hydroxy-1-methyl-propyl, 2-methoxyethyl, 2-ethoxyethyl, 2(2-hydroxy-ethoxy)ethyl, and 2(2(2-hydroxyethoxy)ethoxy)ethyl, especially 2-hydroxyethyl, 2-hydroxypropyl, 2,3,4-trihydroxybutyl and trihydroxy-see.butyl.

Examples of lipophilic $R^{12}$ groups include medium to long chain linear or branched hydrocarbons (e.g. $C_{10}$–$C_{20}$) and aromatic groups, e.g. aralkyl, alkaryl or aryl groups.

Examples of suitable macrocyclic chelants thus include DOTA, DO3A, DOXA, HP-DO3A, TCDA and cyclen and their analogs as well as such chelants linked to targeting molecules or linked to a polymeric backbone to produce a polychelant.

Chelants comprising linear or branched polyazaalkane skeletal units may also be used. These include compounds of formula X

where $X^3$, $R^{12}$ and s are as defined above with at least the terminal $X^3$ of the $[(CR_2^{12})_qX]_y$ moiety being nitrogen, and y is an integer having a value of from 0 to 4, preferably 1, 2 or 3, especially 1 or 2, but $R^{12}$ groups may also together form fused saturated or unsaturated rings on the linker skeleton which may themselves be substituted by metal coordinating groups, $NR_2^{12}$ may represent $N=R^{14}$ where $R^{14}$ is an $C_{1-8}$ alkylidene group optionally substituted as for $R^{12}$, a $N(CR_2^{12})_2N$ bond may optionally be interrupted by a $C_6$ saturated or unsaturated carbocyclic ring, and one nitrogen attached $R^{12}$ group on a non terminal $X^3$ may represent a branching chain $[(CR_2^{15})_qX^3]_mRhu$ $15_2$ and where $X^3$, s and y are as hereinbefore defined and $R^{15}$ is as defined for $R^{12}$ but cannot represent such a branching chain.

Thus imino acid chelants of formula XI $$(R^{12})_3N \qquad (XI)$$

(where $R^{12}$ is as defined above but with the proviso that at least two $R^{12}$ groups carry metal coordinating groups, e.g. $CH_2COOH$, and one links to the dendrimer) may also be used.

The following are examples of preferred polyazaalkane backbone skeletal units for such chelants:

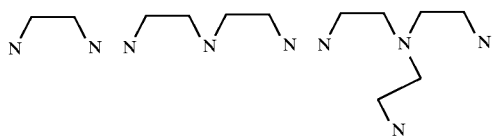

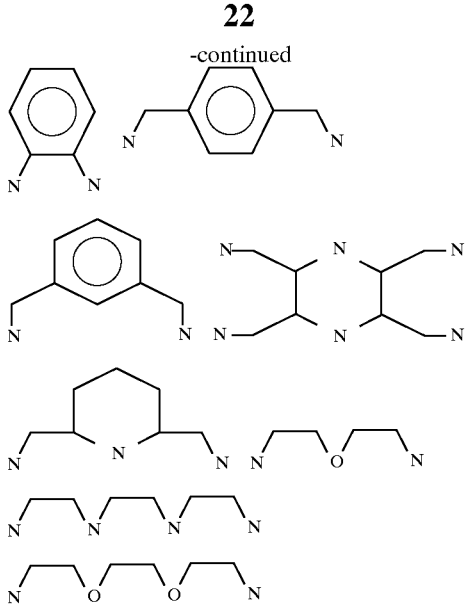

Examples of suitable linear and branched chelants thus include residues of EDTA, DTPA, TTHA, EGTA, EHPG, DPDP, pycac, pycbac, DTPA-BMA, salen, dipeptides (e.g. H-gly-tyr-OH, H-pro-gly-OH, H-gly-ser-OH, H-gly-asp-OH and H-gly-glu-OH), HENSAL, $H_2SHED$, HSALIMH, DFO, PnAO, NTA, HIDPA, LICAM, DEPA, and analogs thereof.

Further examples of chelating agents suitable for attachment to the dendrimeric backbone may be found in the patent literature for MRI contrast agents proposed by the leading companies in that field, namely Nycomed Imaging AS, Nycomed Salutar Inc., Schering AG, Bracco, Guerbet, Mallinckrodt, and Squibb, e.g. U.S. Pat. No. 4,647,447, EP-A-235261, WO-A-89/00557, WO-A-90/08138, WO-A-90/08134, WO-A-91/10669, WO-A-91/15466, WO-A-91/15467, WO-A-92/11232, EP-A-290047, WO-A-90/12050, WO-A-91/05762, WO-A-91/10645, WO-A-92/08707, EP-A-232751, EP-A-292689, WO-A-88/07521, WO-A-88/08422, EP-A-305320, EP-A-331616, etc and the publications listed therein.

Advantageously however the chelant is a polyaminopolycarboxylic acid (PAPCA), preferably a macrocyclic PAPCA and especially preferably the dendrimer backbone is attached to the ring structure of the macrocyclic chelant at a donor ring heteroatom, especially a nitrogen. As an alternative however, the dendrimeric backbone may be linked to a macrocyclic chelant moiety via a linker group attached to the macrocyclic chelant at a ring heteroatom (e.g. a

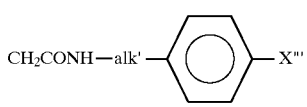

group where alk' is a $C_{1-4}$ alkylene chain and X'" is NCS, $NH_2$, $N_2^+$, NCO, -alk'-COOH, $NHCOCH_2Cl$ or $NHCOCH_2Br$) or at a ring carbon, e.g. as suggested by Meares et al. (see Acc Chem Res 17:202 (1984) and U.S. Pat. No. 4,678,667). Thus, by way of example, a macrocycle such as DO3A may be linked (at the unsubstituted ring nitrogen) using the linker group

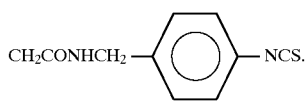

In a preferred alternative oligoaminoacid linkers or linkers serving to produce hydrolysable bonds (such as the diester bonds of WO92/04392) to the chelants may be used.

Similar, conventional chemistry may be used to couple other modifier and active moieties, e.g. PEG molecules or iodoaryl groups, to the dendrimeric backbone.

The magnifiers and bifunctional polychelants of the invention can be used in their unmetallated or undermetallated state for absorption of available metal ions in vivo, such as in metal detoxification. Alternatively, the magnifiers and bifunctional polychelants can be used in their metallated form to deliver chelated metal ions for diagnostic or therapeutic applications.

Metal ions are chosen for chelation by the magnifiers for their ability to perform their diagnostic or therapeutic role. These roles include but are not limited to enhancing images in MRI, gamma scintigraphic or CT scanning, or X-ray, or delivering cytotoxic agents to kill undesirable cells such as in tumors, or for delivering vanadium for the treatment of diabetes etc.

Metals that can be incorporated, through chelation, include lanthanides and other metal ions, including isotopes and radioisotopes thereof, such as, for example, Mg, Ca, Sc, Ti, B, V, Cr, Mn, Fe, Co, Ni, Cu, Zn, Ga, Sr, Y, Zr, Tc, Ru, In, Hf, W, Re, Os, Pb and Bi. Particularly preferred radioisotopes of some of the foregoing include $^{153}$Sm, $^{64}$Cu, $^{67}$Cu, $^{67}$Ga, $^{68}$Ga, $^{89}$Sr, $^{88}$Y, $^{90}$Y, $^{99m}$Tc, $^{97}$Ru, $^{103}$Ru, $^{111}$In, $^{186}$Re, $^{188}$Re, $^{203}$Pb, $^{211}$Bi, $^{212}$Bi, $^{213}$Bi, and $^{214}$Bi. The choice of metal ion for chelation by polychelants of the invention will be determined by the desired therapeutic or diagnostic application.

For use with radionuclides, such as in nuclear medicine, this invention provides the advantage of tight binding of the radionuclides by the macrocyclic chelants. This allows a more specific image due to lower background levels of the metals.

The bifunctional dendrimeric compounds of the invention involve coupling the magnifier to a site-directed molecule. The site-directed molecules may be any of the molecules that naturally concentrate in a selected target organ, tissue, cell or group of cells, or other location in a mammalian body, in vivo. These can include amino acids, oligopeptides (e.g. hexapeptides), molecular recognition units (MRU's), single chain antibodies (SCA's), proteins, Fab fragments, and antibodies. Examples of site-directed molecules include polysaccharides (e.g. hyaluronic acid, chitosan, agarose, cellulose, starch, dextran, alginate, glucan, keratan sulphate, dermatan sulphate, chondroitin sulphate, heparan sulphate, heparin, inulin, and collagen), bile acids, lipids and derivatives thereof (e.g. FA, phospholipids, glycolipids, and cholesterol), proteins (such as wheat germ agglutinin, complement components, complement component fragments, cytokines, eicosanoids, fibronectin, ferritin, transferrin, hemoglobin, EGF (epidermal growth factor), mannose-6-phosphate, ligands, lectins, asialofetuin, polyclonal IgG, blood clotting proteins (e.g. hirudin), lipoproteins and glycoproteins), hormones, growth factors, nucleic acids, deoxyribonucleic acids, antigens, haptens, and clotting factors (such as PF4). Exemplary site-directed proteins include polymerized fibrin fragments (e.g., $E_1$), serum amyloid precursor (SAP) proteins, low density lipoprotein (LDL) precursors, serum albumin, surface proteins of intact red blood cells, receptor binding molecules such as estrogens, liver-specific proteins/polymers such as galactosyl-neoglycoalbumin (NGA) (see Vera et al. in Radiology 151: 191 (1984)) N-(2-hydroxypropyl) methacrylamide (HMPA) copolymers with varying numbers of bound galactosamines (see Duncan et al., Biochim. Biophys. Acta 880:62 (1986)), and allyl and 6-aminohexyl glycosides (see Wong et al., Carbo. Res. 170:27 (1987)), and fibrinogen.

The site-directed protein can also be an antibody or a fragment thereof or a small site-specific peptide. The choice of antibody, particularly the antigen specificity of the antibody, will depend on the desired use of the conjugate. Monoclonal antibodies are preferred over polyclonal antibodies.

Human serum albumin (HSA) is a preferred protein for the study of the vascular system. HSA is available commercially from a number of sources including Sigma Chemical Co. Preparation of antibodies that react with a desired antigen is well known. Antibody preparations are available commercially from a variety of sources. Fibrin fragment $E_1$ can be prepared as described by Olexa et al. in J. Biol. Chem. 254:4925 (1979). Preparation of LDL precursors and SAP proteins is described by de Beer et al. in J. Immunol. Methods 50:17 (1982). The above described articles are incorporated herein by reference in their entirety.

Methods for attaching backbone polymers to antibodies and other proteins are within the level of skill in the art. Such methods are described in Pierce 1989 Handbook and General Catalog and the references cited therein, Blatter et al, Biochem., 24:1517 (1985) and Jue et al, Biochem., 17:5399 (1978). The references cited above are incorporated herein by reference in their entirety.

In the bifunctional dendrimeric compounds, preferably one or two backbone molecules are linked to the site-directed molecule. By limiting the number of magnifiers linked to the site-directed molecule, the pharmacological behavior of the bifunctional dendrimeric compound would be expected to show high target specificity and low non-specific binding.

The bifunctional dendrimeric compounds are capable of containing a large number of active (e.g. chelant moieties). This allows site-specific imaging to be enhanced beyond the levels previously available.

These magnifiers and bifunctional polychelants are not only extremely useful for magnetic resonance and X-ray imaging, they are also useful in other forms of imaging, as well as in nuclear medicine. Osmolality of currently available image enhancing agents contributes to some of the undesirable side effects of these agents, including pain to the patient. By allowing a marked increase in the number of image enhancing chelated metal centres per molecule in solution, this invention allows for a significant decrease in osmolality, while retaining the same level or increasing the level of image enhancement.

In general, magnifiers are synthesized by conjugating the active moieties to the backbone molecule prior to conjugating the backbone molecule to any large modifier moiety such as PEG or a site-directed macromolecule. In most cases, the reaction conditions used for joining the chelants to the backbone molecule would denature proteins. Therefore, to preserve its tertiary structure and biological function an antibody or other site-directed protein will not generally be conjugated to a backbone molecule before the chelant groups have been loaded onto that backbone molecule, unless of course this can be done without denaturing the protein. The metal ions can be added to form the metal complex of the polychelants prior to or following conjugation of the magnifier to the modifier (e.g. site-directed macromolecule). Preferably, the metal will be added prior to conjugation of the magnifier polychelant to most proteins, particularly antibodies, in particular to avoid adventitious binding of the metal to the protein. However, for some metal ions such as radionuclides with a short half-life, metallation will preferably be performed following conjugation, just prior to use.

In general, known methods can be used to join the chelants to backbone molecules. Such methods include for example the mixed anhydride procedure of Krejcarek et al. (Biochemical and Biophysical Research Communications 77: 581 (1977)), the cyclic anhydride procedure of Hnatowich et al. (see Science 220: 613 (1983) and elsewhere), the backbone derivatisation procedure of Meares et al. (see Anal. Biochem. 142: 68 (1984) and the method described by Manabe et al. in Biochemica et Biophysica Acta 883: 460–467 (1986) for attaching DTPA residues onto a poly-L-lysine backbone using a modification of the cyclic anhydride procedure. While for preferred macrocyclic chelants, such as DOTA, the conventional mixed anhydride and cyclic anhydride conjugation techniques described by Krejcarek and Hnatowich are ineffective, it has been found that modifying the mixed anhydride procedure by reacting a polycarboxylic macrocyclic chelant in an anhydrous medium with an amine base of sufficient strength to abstract all the carboxyl protons (i.e. a high enough pKa) yields an amine salt which can react with an alkylhaloformate to produce an activated anhydride capable of conjugating to the backbone polyamine without causing the undesired cross-linking associated with prior art bifunctional polychelants. For most macrocyclic chelants tetramethylguanidine or an amine base of similar strength will be the preferred base.

More complex conjugation techniques, involving for example the use of backbone derivatized macrocyclic chelants in a manner analogous to that of Meares et al. (supra), may of course be used but the increased cost and complexity of the overall production makes this a less desirable route. Similarly the chelants can be attached to the backbone polymer by a haloacetylhalide, a phosgene or a thiophosgene method depending on the available reactive group on the chelating agent.

For chelants eg. macrocycles with a pendant carboxylate, including but not limited to DOTA, TETA, TRITA (1,4,7, 10-tetraazacyclotridecanetetraacetic acid) and NOTA, one of the carboxylates can form an entity which can react with a primary amine group of the backbone polymer. Methods of forming a reactive entity from a carboxylate group include the modified mixed anhydride reaction for example using isobutylchloroformate (IBCF), or the formation of an "activated ester" using a carbodiimide (DCC or EDAC, cf. Pierce Catalog (1988), pages 252 and 253). Both reaction sequences give rise to a backbone polymer multiply substituted with the chelant moieties through stable amide linkages. The modified mixed anhydride method however is the preferred method for use in joining carboxylate-containing macrocyclic chelants to the backbone polymer.

The modified mixed anhydride reaction is performed in an anhydrous solvent preferably with a melting point below 5° C., cooled to a temperature not lower than 5° C. or greater than about 55° C. above its freezing point. The solubilization of the chelant in the appropriate solvent is conveniently effected by preparation of the amine salt of the chelant using the amine base in situ.

The choice of base is determined by the pKa of the relevant carboxylates. For most chelants, tetramethylguanidine (TMG) is especially preferred. In general, bases will conveniently be selected from those bases whose pKa value exceeds the highest pKa of the chelant by at least 0.5, preferably 0.8, especially preferably at least 1.0. Amine bases having pKa's of at least 11, especially at least 11.3, particularly at least 12, are particularly preferred and besides TMG particular mention may be made of piperidine, quinuclidine and N-ethylpiperidine and more especially DBU (1,8-diazabicyclo[5.4.0]undec-7-ene) and DBN (1,5-diazabicyclo(4.3.0)non-5-ene). Further bases are listed by Martell and Smith in "Critical Stability Constants" Vol. 5, first supplement, Plenum Press, NY 1982.

The appropriate quantity of neat (chilled) alkylhaloformate is now added with stirring and the original temperature of the solvent is maintained by cooling, e.g. by addition of coolant, if required. Isobutylchloroformate is especially preferred. The resulting activated anhydride of the chelant can be reacted with an amine-containing dendrimer to form a magnifier polychelant. The magnifier polychelant, for most applications, is metallated at this point and purified by chromatography or crystallization to remove excess metal ions and lower molecular weight metal complexes. For use with target-specific molecules the magnifier polychelant, or the at least partially metallated form thereof, still containing at least one free amine, is conjugated to the targetting molecule, for example by reaction with one of many well-known heterobifunctional coupling agents. In situations where prior metallation is not appropriate, e.g. with radionuclide metal ions with short half-lives, the bifunctional polychelant can be prepared using a metal-free magnifier and coupling as described above, followed by metallation (vide infra) and final rapid, simple purification by chromatography or filtration.

The chelants can also be linked to the backbone polymer through a non-coordinating primary amine group or a remote carboxyl group not involved in metal coordination. Macrocyclic chelants having a non-coordinating primary amine group include primary amine side-chain-derivatized DOTA macrocycles, primary amine-derivatized DO3A, and primary amine-derivatized hexaaza and octaaza macrocycles and macrobicycles (the HAMs, sepulchrates and sarcophagines) as well as the broad class of derivatized crown ether cryptates. Where carboxyl groups on the chelant (or indeed on any other active moiety) are used for linkage, routine carboxyl activation chemistry can be used for attachment for example to amine functions on the backbone or on a linker conjugated to the backbone.

The non-coordinating primary amine group on these chelants can be reacted with a haloacetylhalide under well-known conditions to form a haloacetamide. The haloacetamide can react with a primary amine of the backbone polymer to form a stable amide linkage between the chelant and the polymer. The haloacetylhalide method described in De Riemer et al, J. Labelled Compd. Radiopharm. 18:1517 (1981) can be used to join amine-containing chelants to the backbone polymer.

Amine groups on a chelant can also be reacted with phosgene to generate a reactive isocyanate group, or with thiophosgene to generate a reactive isothiocyanate group. Those groups can react with a primary amine of the backbone polymer to form a stable urea or more stable thiourea linkage, respectively, between the ligand and the backbone polymer,. Gansow, Inorg. Chimica Acta 91:213 (1984) and Moi et al, J. Amer. Chem. Soc. 110:6266 (1988) describe methods of linking chelants to proteins having an amine group through formation of the isocyanate or isothiocyanate moieties using the phosgene or thiophosgene methods, respectively. See also Desreux, Inorg. Chem. 19:1319

(1980); Bryden et al, Anal. Chem 53:1418 (1981); Delgardo et al, Talanta 29:815 (1982); Cacheris et al, Inorg. Chem. 26:958 (1987); Moi et al., Inorg. Chem 26:3458 (1987) and Meares et al, Acc. Chem. Res. 17:202 (1984).

Still further means of coupling the chelant moieties to the backbone polymer are illustrated by the following reaction schemes:

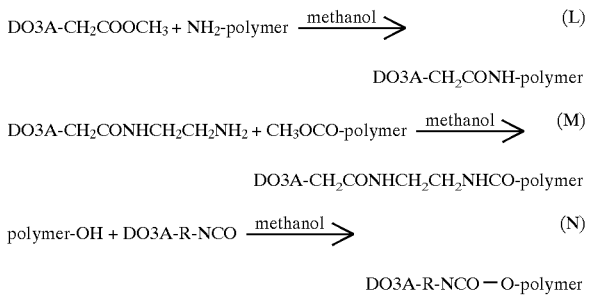

For amine terminating dendrimeric polymers the materials $NH_2$--polymer and $CH_3OCO$--polymer respectively represent full and half generation (eq. $G_{2.0}$ and $G_{2.5}$) dendrimers.

The interposition of an oligoamino acid (e.g. oligolysine) chain in the polymer to active (or modifier) moiety linkage is particularly desirable as this provides the capacity for controlled in vivo hydrolytic release of the active moiety.

As indicated earlier the choice of metal ions to be chelated by the polychelants of the invention depends upon the diagnostic or therapeutic technique for which the resulting polychelate is to be used. For MRI, the metal ions should be paramagnetic, and preferably non-radioactive. For X-ray and ultrasound imaging, heavy metal ions, e.g. with atomic numbers of at least 37, preferably at least 50, should be used, again preferably non-radioactive species. For scintigraphy or radiotherapy the metal ions should of course be ions of radioactive isotopes. For thermotherapy, one may use chelating groups to attach to the dendrimer iron oxides or other superparamagnetic polyatomic species which are capable on external application of alternating magnetic fields or MW radiation of producing a localized heating effect. Such materials may equally be used in MR, X-ray, EIT or magnetometric imaging.

Methods of complexing metal ions with chelants and polychelants are within the level of skill in the art. Each of the metals used can be incorporated into a chelant moiety by one of three general methods: direct incorporation, template synthesis and/or transmetallation. Direct incorporation is preferred.

Preferably, metal incorporation into bifunctional polychelants is accomplished prior to attachment of the magnifier(s) to a site-directed molecule. The metal is titrated from sub-stoichiometric levels up to full incorporation, thus eliminating the need for dialysis and extensive chromatographic purification. In this manner significant losses as well as dilution are avoided. Non-specific binding of the metal ions to the site-directed molecules is also prevented. However, application of the invention to radionuclides with short half-lives may require metallation of the bifunctional polychelant as a final step, followed by simple rapid purification (e.g. gel filtration) to remove excess unbound radionuclide.

The metal ions Fe(III), Cr(III), Mn(II), Hg(II), Pb(II), Bi(III) and the lanthanides can be directly incorporated into polyaminopolycarboxylates by the following general procedure. A water-soluble form of the metal, generally an inorganic salt, is dissolved in an appropriate volume of distilled, deionized water. The pH of the solution will be below 7. An aqueous solution containing an equimolar amount of the polychelant is added to the metal solution at room temperature while stirring. The pH of the mixture is raised slowly by addition of base, typically 0.1M NaOH, until the donor groups of the polychelant are deprotonated, generally in the pH range of 5 to 9, depending on the chelant moieties. Particular care must be taken with the lanthanide ions to maintain the pH below 8 to avoid precipitation of the metal hydroxide. Metal incorporation into DOTA derived and related macrocylic chelant moieties will normally be a slow process, as described in the references cited below. Specific examples of the procedure are contained in the following references.

Choppin et al, J. Inorg. Nucl. Chem., 33:127 (1971), Margerum, Rec. Chem. Prog., 24:237 (1973) and D'Olieslager et al, J. Inorg. Nucl. Chem., 35:4255 (1973) describe direct incorporation of the lanthanides into polyaminopolycarboxylates. Margerstadt, Mag. Res. Med., 3:808 (1986) and WO-A-87/06229 describe incorporation of Gd(III) into DOTA. A method of preparing Bi and Pb complexes of DOTA is described by Kumar et al, J. Chem. Soc. Chem. Commun., 3:145 (1989). The above references are incorporated herein by reference in their entirety.

Direct incorporation of Hf, Zr, W, Hg and Ta can be performed according to well known methods. See, for example, U.S. Pat. No. 4,176,173 (Winchell).

Transmetallation is useful when the metal ion needs to be reduced to a more appropriate oxidation state for the donor atoms of the chelant moiety to bind. For example, to incorporate $^{99m}$Tc or $^{186/188}$Re, the metal ion must be reduced to Tc(V) or Re(V) by the use of reducing agents such as $SnCl_2$ or cysteine by well known methods. This method requires formation of an intermediate complex. A typical example is the reduction of $^{99m}$Tc with Sn in the presence of a weakly coordinating ligand such as glucoheptonate prior to complexation with chelants such as DOTA. These methods are well known in the radiopharmaceutical art. $^{67}$Cu utilizes tetraamine chelates such as tet A or tet B (see Bhardaredj et al., JACS, 108:1351 (1986)) to stabilize Cu(II) for reaction with stronger-binding chelants.

The metal chelates of the polychelants of the invention may be administered to patients for imaging in amounts sufficient to yield the desired contrast with the particular imaging technique. Generally dosages of from 0.001 to 5.0 mmoles of chelated imaging metal ion per kilogram of patient bodyweight are effective to achieve adequate contrast enhancements. For most MRI applications preferred dosages of imaging metal ion will be in the range from 0.001 to 1.2, e.g. 0.02 to 0.5, mmoles/kg bodyweight while for X-ray applications dosages of from 0.5 to 1.5 mmoles/kg are generally effective to achieve X-ray attenuation. Preferred dosages for most X-ray applications are from 0.8 to 1.2 mmoles of the lanthanide or heavy metal/kg bodyweight.

Where a dendrimeric compound according to the invention is required to collect in the blood pool, then preferably a higher generation dendrimeric backbone will be used, for example a fourth to sixth generation dendrimeric backbone. Alternatively a lower generation backbone may be used which carries modifiers (e.g. PEG molecules) which serve to bring the overall molecular weight up and should prevent or decelerate renal clearance. Such polychelants have enhanced relaxivity compared to known blood pooling and ECF contrast agents and thus a lower effective dosage can be administered.

For X-ray applications, to extend the photon energy range over which the polychelates of the invention are optimally effective the polychelates used may be of two or more different metals, either as mixtures of homopolychelates or as a heteropolychelate.

The production and loading of iodinated moieties onto a dendrimeric backbone (D) can thus be illustrated by the following reaction schemes:

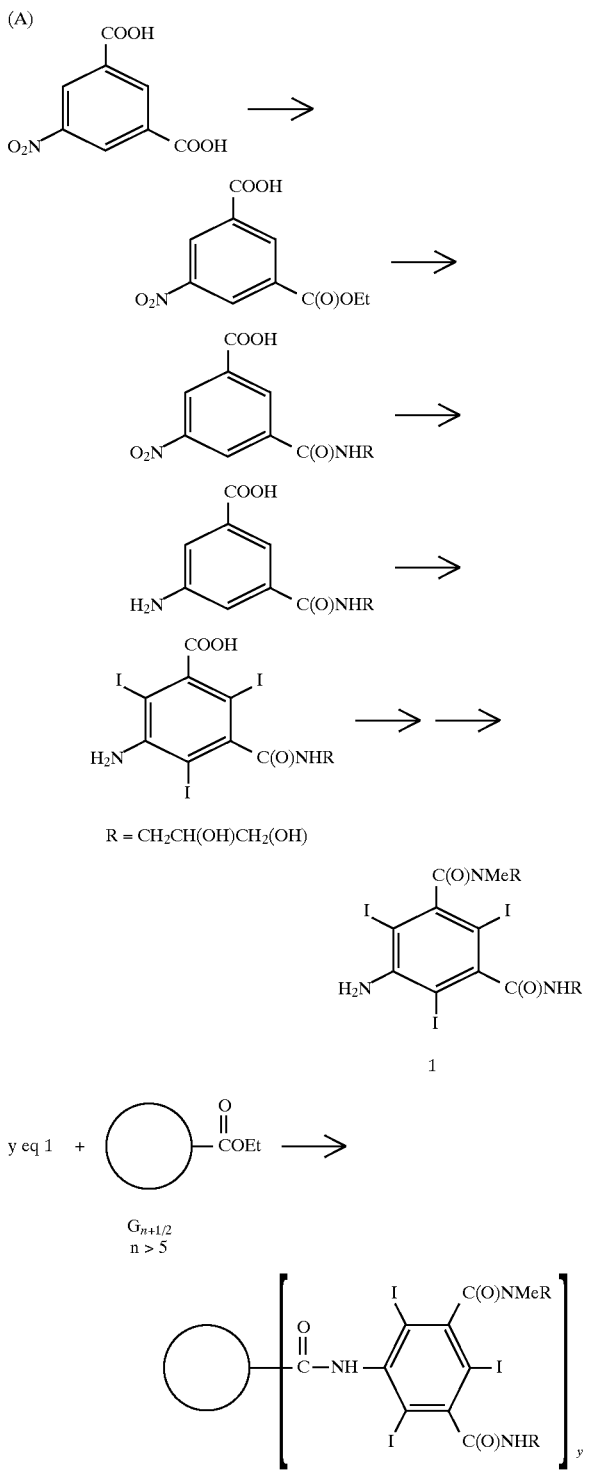

(where y is the loading level of the resultant dendrimer, e.g. 2 to 200, preferably 5 to 150, especially 50 to 110). The resultant compounds will possess high water solubility and low osmolality, will incorporate analogues of approved CT agents with low toxicity and would carry a large number of iodine atoms per molecule, e.g. 288 for a $G_5$ dendrimer.

Alternatively iodine could be attached directly to the termini of the dendrimers by conventional chemistry, e.g. by treating a hydroxy terminating dendrimer (e.g. D-(CONHCH$_2$CH$_2$OH)$_n$, where D is for example 5th or greater generation) with tosyl chloride to yield the polytosylate which on treatment with sodium iodide yields the polyiododendrimer (e.g. D-(CONHCH$_2$CH$_2$I)$_n$). Where protein-binding inhibiting modifier moieties are conjugated to the dendrimeric framework, optionally via biodegradable bonds or linkers, a step-wise construction might include: 1) preparation of a dendrimeric backbone loaded with active moieties (e.g. metal chelates) of MW substantially less than the globular cut-off (<50 kD) preferably less than 30 kD especially less than 20 kD; 2) attachment of an oligomeric or polymeric modifier to provide a steric barrier to protein binding.

The modifier may for example be PEG, PPG, polydextran, or a polysaccharide (for example, amylase, amylopectin, starch, heparin or glycogen). Each modifier will preferably be below 20 kD and, more preferably, below 10 kD. A brush structure, i.e. a magnifier loaded with an array of protein binding inhibiting modifiers requires several modifiers per magnifier. The modifiers should preferably be attached to 2–50% of the dendrimer attachment sites. A major advantage is avoiding the RES (liver, spleen and bone macrophage uptake). A modifier such as PEG may dramatically increase plasma $t_{1/2}$ and the utility of a blood pool agent.

A commercial agent based on any metal chelate should minimize free metal release and tissue retention. The longer any agent remains in blood, the more likely it will release metal. This is especially true for any acyclic ligands; DOTA or DO3A derived chelant moieties are kinetically inert to metal release at physiological pH and are preferred as blood pool agents.

An additional way to make modified magnifiers is to use hydrolytically sensitive bonds between the modifier (e.g. PEG) and the magnifier. PEG will still act as a steric barrier, and the extended circulation time may lead to biodegradation into small PEG's and one magnifier. In addition, biodegradability of an agent adds a margin of improvement if some organ uptake occurs. All of the fragments will be renally excreted from the blood or ECF and more rapidly flushed from the liver into the bile and faeces.

The dendrimeric backbone to the protein-binding inhibiting modifier-carrying magnifiers is preferably a polymer with MW<40 KD. The polymer must provide multiple functional groups for attachment of diagnostic or therapeutic agents, and may include functionality for attachment to a targeting group (antibody, protein, peptide, etc.). optionally the polymer is a low generation (e.g. Generation 2,3,4) dendrimers, partially loaded with active moieties and modified with PEG or other protein binding inhibitors to bring the total size/molecular weight up to 40–100 KD (size based on globular proteins). In this way, an exit via the kidneys is possible on a reasonable time scale, while avoiding liver uptake.

Any aspect of biodegradation, such as biodegradable cores, serves to enhance total body clearance of the agent. Stable attachment of PEG to a biodegradable magnifier or unstable attachment of PEG (via a hydrolytically sensitive bond) to a stable magnifier would be appropriate. However, biodegradable magnifiers may advantageously increase the safety margin if small amounts are distributed to the liver. The biodegradable cores are metabolized more rapidly. This decreases the time of exposure of the metal chelates to low pH and liver enzymes.

Amine core dendrimers or alternatively biodegradable dendrimers with a multitude of amines on the surface may be preferred. The best blood half life is found by adjusting the backbone's molecular weight and the loading levels of the active and modifier moieties. Generations from one to five (MW=1000–25,000) are preferred backbones. Generations with the most amine sites within this range are preferred (e.g. with total terminal amines=24,48 or 96).

The protein binding modifiers include water soluble linear oligomers/polymers such as polyethers, polyols, and polysaccharides. Preferred such modifiers include polyethyleneoxide, polyethyleneglycol, or monomethyl polyethyleneglycol of MW between 200 and 10,000. Loadings of such oligomers/polymers onto the dendrimeric backbone is advantageously at 2–50% of the available attachment sites. For example, multiple numbers of PEG molecules of molecular weight 500–10,000 may be attached to obtain a total MW of >40,000. An upper molecular weight limit would be dependent on the incorporation of cleavable PEG groups and/or biodegradable dendrimers. Greater than 50% loading of such modifiers may undesirably dilute the active moiety content, block the magnifier surface and be difficult to achieve due to steric restraints.

There are many methods available for attachment of polyethyleneglycol or monomethylpolyethylene glycol to polyamines or other functional dendrimer backbones. Attachment may for example be accomplished through an inert covalent linkage or through a biodegradable attachment (e.g. carbamate). The methodology for such attachment can be found in the following references: Harris, Rev. Macromol. Chem. Phys. C25(3):325 (1985), and Delgado, Critical Rev. Drug Carrier Sys. 9(3,4):249 (1992). Thus an exemplary scheme is as follows:

General Methods to Construct a Modifier-loaded Compound: $H_2N$—R is an amino group on the dendrimeric backbone that may or may not have active moieties (e.g. metal chelates) already attached. MePEG-X is methoxy terminated PEG of molecular weight 500–10,000.

Possible routes using PEG Attachment Chemistry

1. Cyanuric chloride route: Coupling conditions=pH 9, reaction with thiols, possible dimerization with mono derivative, UV chromophore.

Reactions:

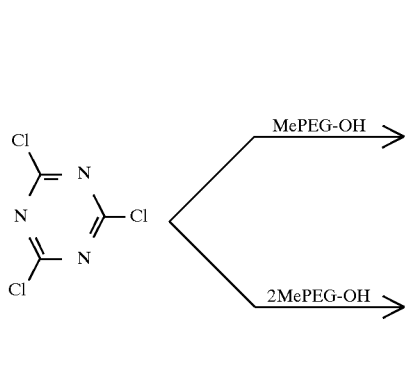

(see for example Anal. Biochem. 165:114 (1987) and J. Biol. Chem. 252:3582 (1977)).

2. Route leading to a Amide bond between PEG and magnifier: unreactive with thiols, possible ester hydrolysis with succinic derivative.

Reactions:

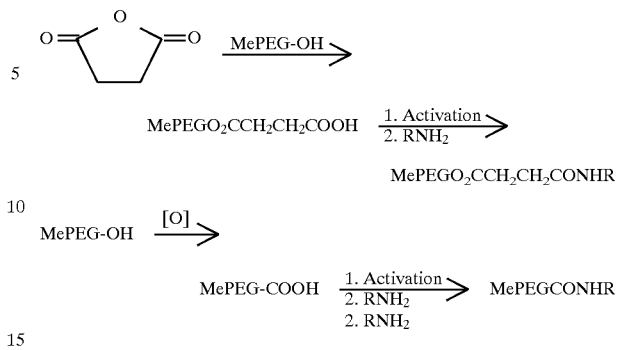

(see for example Appl. Biochem. Biotechnol. 11:141 (1985) and Cancer Biochem. Biophys. 7:175 (1984)).

3. Carbamate bond between PEG and magnifier: Long reaction time, coupling conditions=pH 8.5–9.2, appreciable hydrolysis, activated PEG can be stored.

Reactions:

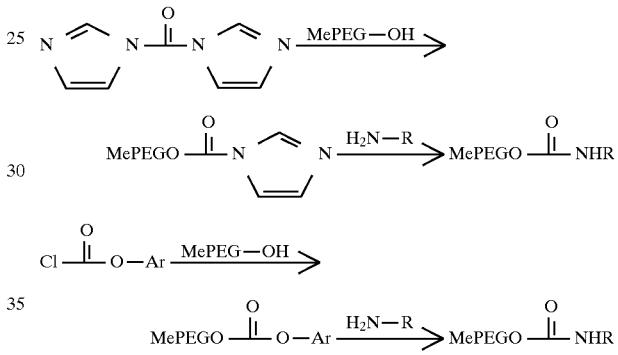

(see for example Klin. Paediatr. 200:184 (1988)) and Anal. Biochem. 131:25 (1983)).

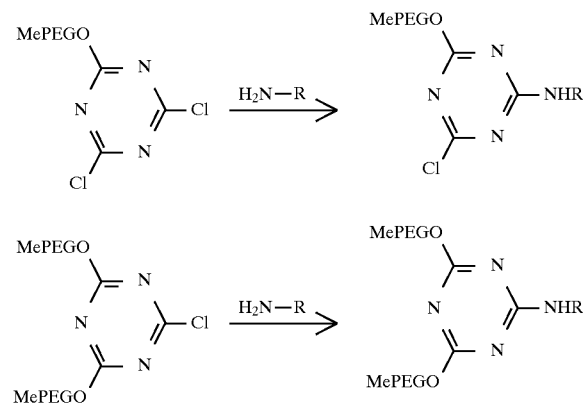

4. Attachment with sulfonyl chlorides: Mild conditions (pH 7.5, ambient temperature), rapid reaction Reactions:

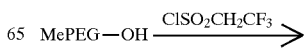

-continued

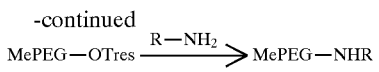

(see for example Biotechnol. Appl. Biochem. 12:119 (1990)).

5. Amine Linkage: Very stable linkage.
Reactions:

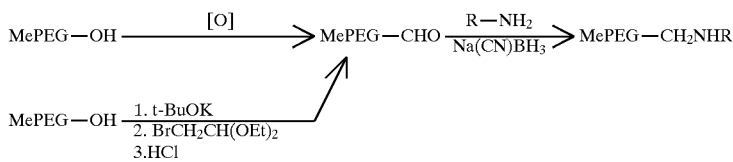

(see for example J. Macromol. Sci., Rev. Poly. Chem. Phys., C25:325 (1985) and J. Polymer Sci. 22:341 (1984)).

Routes to PEG loaded Magnifiers

A) React PEG first

B) React DO3A first
Use less than stoichiometric amount of chelate
(< y to leave open sites for attachment of several PEG moeties

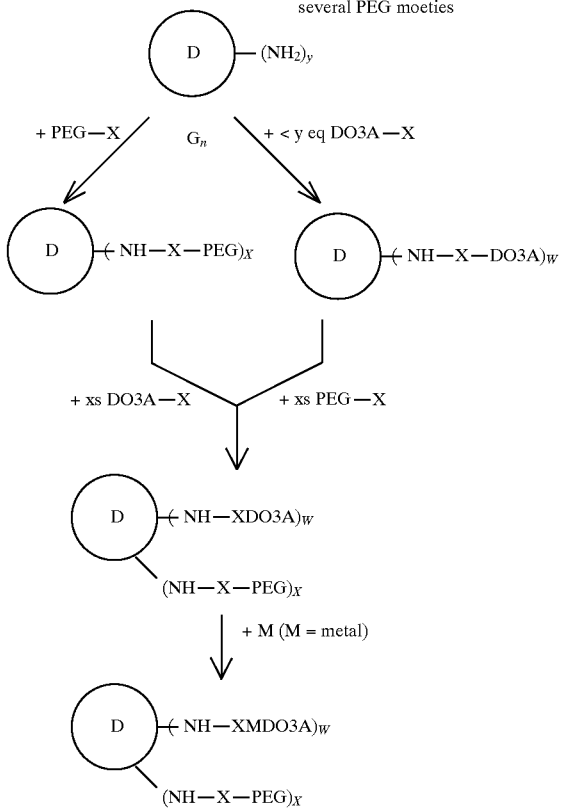

Much of the above discussion has focused on the polychelants of the invention. Where the active moieties are not in chelate form then they may be presented in the same or lower dosages than those at which they are normally administered, e.g. 1/5 to 1/1 of the normal dosage, and for diagnostic agents even at higher than normal dosages. Thus for example for iodinated compounds for use as X-ray contrast agents, overall iodine concentrations of 50 to 1000, e.g. 150 to 500 mgI/ml may be contemplated.

The compounds of the present invention may be formulated with conventional pharmaceutical or veterinary aids, for example emulsifiers, fatty acid esters, gelling agents, stabilizers, antioxidants, osmolality adjusting agents, buffers, pH adjusting agents, etc., and may be in a form suitable for parenteral or enteral administration, for example injection or infusion or administration directly into a body cavity having an external escape duct, for example the gastrointestinal tract, the bladder or the uterus. Thus the compounds of the present invention may be in conventional pharmaceutical administration forms such as tablets, capsules, powders, solutions, suspensions, dispersions, syrups, suppositories etc.; however, solutions, suspensions and dispersions in physiologically acceptable carrier media, for example water for injections, will generally be preferred.

The compounds according to the invention may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized. Suitable additives include, for example, physiologically biocompatible buffers (as for example, tromethamine hydrochloride), additions (e.g., 0.01 to 10 mole percent) of chelants (such as, for example, DTPA, DTPA-bisamide or non-complexed magnifier polychelant) or calcium chelate complexes (as for example calcium DTPA, CaNaDTPA-bisamide, calcium-magnifier polychelant or CaNa salts of magnifier polychelants), or, optionally, additions (e.g., 1 to 50 mole percent) of calcium or sodium salts (for example, calcium chloride, calcium ascorbate, calcium gluconate or calcium lactate combined with metal chelate complexes of magnifier ligands, and the like).

If the compounds are to be formulated in suspension form, e.g., in water or physiological saline for oral administration, a small amount of soluble chelate may be mixed with one or more of the inactive ingredients traditionally present in oral solutions and/or surfactants and/or aromatics for flavoring.

For MRI and for X-ray imaging of some portions of the body the most preferred mode for administering metal chelates as contrast agents is parenteral, e.g., intravenous administration. Parenterally administrable forms, e.g., intravenous solutions, should be sterile and free from physiologically unacceptable agents, and should have low osmolality to minimize irritation or other adverse effects upon administration, and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions can maintain preservatives, antimicrobial agents, buffers and antioxidants conventionally used for parenteral solutions, excipients and other additives which are compatible with the chelates and which will not interfere with the manufacture, storage or use of products.

Viewed from a further aspect the invention provides a diagnostic or therapeutic composition comprising a dendrimeric compound of the invention or a salt thereof together with at least one pharmaceutical carrier or excipient.

Viewed from a still further aspect the invention provides the use of a dendrimeric compound according to the invention or a salt thereof for the manufacture of a diagnostic or therapeutic composition.

Viewed from another aspect the invention provides a method of generating an image of a human or non-human animal, especially mammalian, body which method comprises administering to said body an image enhancing amount of a dendrimeric compound according to the invention or a salt thereof and thereafter generating an image e.g. an MR, X-ray, ultrasound, EIT or scintigraphic image, of at least a part of said body.

Viewed from a still further aspect the invention provides a method of therapy of the human or animal body said method comprising administering to said body a therapeutically effective amount of a dendrimeric compound according to the invention.

Viewed from a yet still further aspect the invention provides a method of producing a dendrimeric compound according to the invention, said method comprising conjugating a plurality of therapeutically or diagnostically active moieties (e.g. macrocyclic chelants) to a dendrimeric polymer, e.g. a polyamine, and optionally metallating the resulting compound, and optionally conjugating to biodistributlon modifier (e.g. PEG or a site-specific molecule).

The dendrimeric polymer used in this method is preferably up to 8th generation, eg. up to 7th, particularly 4th, 5th or 6th, generation. The generation desired will of course depend upon the number of active and modifier moiety attachment sites desired, on the linker moieties used and on the overall size, molecular weight and configuration desired which will in turn be dependent to some degree on the desired end use for the dendrimeric compound.

Viewed from another aspect the invention provides a detoxification composition comprising a polychelant according to the invention or a weak chelate complex or salt thereof with physiologically tolerable counterions, together with a pharmaceutical carrier or excipient.

Viewed from a still further aspect, the invention provides a method of metal detoxification comprising administering to a human or non-human animal a detoxifying amount of a polychelant according to the invention or a weak chelate complex or salt thereof with physiologically tolerable counterions.

The protein binding inhibitor loading of dendrimeric compounds is iteself novel and in a further aspect the invention provides a dendrimer compound comprising a dendrimeric backbone moiety with linked thereto a plurality of diagnostically or therapeutically active moieties (e.g. chelant moieties capable of complexing metal ions), characterised in that said backbone moiety has linked thereto a plurality of protein binding inhibiting moieties, e.g. PEG residues.

This invention is further illustrated by the following specific but non-limiting examples. Temperatures are given in degrees Celsius and concentrations as weight percentages unless otherwise specified.

EXAMPLE 1

Preparation of DTPA-dendrimer Magnifier

A slurry of DTRPA (16.8 g, 42 mmol) in acetonitrile (150 mL) was treated with TMG (50 mL). The mixture was stirred under nitrogen at ambient temperature until dissolution was complete then cooled to −30° C. Isobutyl chloroformate (1.5 mL, 12 mmol), was added dropwise. After stirring at 0° C., a solution of phosphazene Go (Example 3a) (0.22 g, 0.04 mmol) in DMF (20 mL) and TMF (40 mL) was added dropwise over a period of 1½ hours. The mixture was stirred at ambient temperature for 16 hours, evaporated to dryness, dissolved in $H_2O$ (100 mL) and dialyzed against 0.2M oxalic acid (3×3 L) for 6 hours and 0.2M $NaHCO_3$ (2 L) overnight. The crude material was purified by medium pressure chromatography (2.5×20 cm Sephadex G-25, refractive index detection). The loading 25% was calculated from the integral intensities in the $^1H$ NMR.

EXAMPLE 2 a) Preparation of p-nitrobenzylchloroacetamide

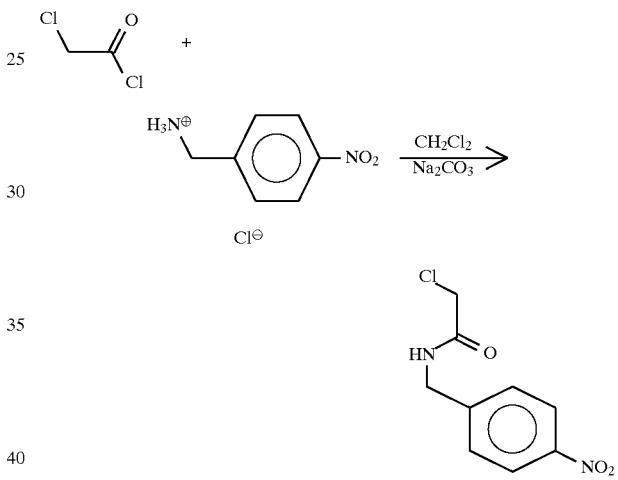

Para-nitrobenzylammonium chloride (1.18 g, 6.2 mmol) and $Na_2CO_3$ (1.31 g, 12.5 mmol) were placed in flask and methylene chloride (200 mL) added. The solution was heterogeneous so 5 mL water was added to give a two-phase system. Chloroacetylchloride (0.50 mL, 6.2 mmol) was added via syringe at ambient temperature and the solution turned milky white immediately. After stirring for 15 minutes the organic layer was light yellow. After 45 minutes more water was added (5 mL) which gave a clear aqueous layer. The layers were seperated and the aqueous layer washed with $CH_2Cl_2$ (50 mL). The combined organic phases were dried over $MgSO_4$ and the volatiles removed. The crude product was taken up in $CHCl_3$/methanol (6:1) and passed through silica. Removal of volatiles gave the title product as a yellow solid in 98% yield.

b) Preparation of tris-tertbutyl D03A-(p-nitrobenzyl) amide

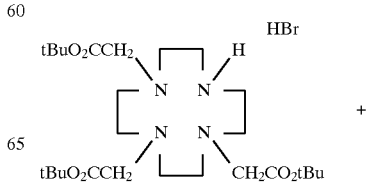

-continued

ClCH₂CONHCH₂(pNO₂—C₆H₄) $\xrightarrow{\text{DMF}}{\text{K}_2\text{CO}_3}$

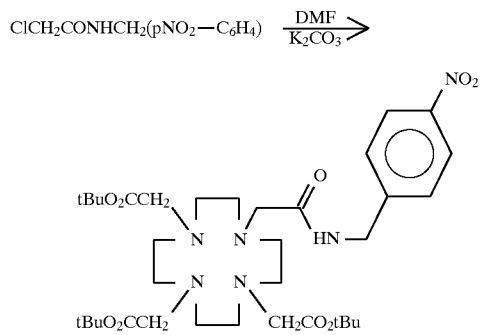

Under nitrogen gas, tris tert.butyl-DO3A-HBr (0.68 g, 1.1 mmol) was dissolved in dimethylformamide (100 mL). An excess of sodium carbonate was then added resulting in a white slurry. In a separate flask, dimethylformamide (75 mL) was added to para-nitrobenzylchloroacetamide (Example 2(a), 0.25 g, 1.1 mmol) and this solution was added via cannula to the tris t-butyl DO3A. A small amount of NaI (20 mg) was added to accelerate the reaction. The reaction appeared heterogeneous so K₂CO₃ (which is more soluble than the sodium analogue) was added and the reaction allowed to stir at ambient temperature for 20 hours. Water (100 mL) was added, the solution warmed and toluene (200 mL) was added. The layers were separated and the organic phase dried over MgSO₄. The crude product was isolated and ¹H and ¹³C NMR indicated only one product. Flash chromatography on a Si column (5:1 CHCl₃:CH₃OH) yielded pure title product. (MH⁺=707.5 and MH–Na⁺=729.5 found).

c) Preparation of DO3A-(p-nitrobenzyl)amide 0.7 g (0.01 mmol) of the tris t.butyl ester of Example 2(b) was dissolved in methylene chloride (20 mL) to give a light yellow solution. TFA (approx. 10 mL) was added in small aliquots at ambient temperature. After 1 hour, the solution appeared to be a bit more yellow. After 1½ hours, the volatiles were removed in vacuo. This procedure was repeated six times but with smaller amounts of methylene chloride (10–15 mL). Following the last treatment with CH₂Cl₂/TFA, the volatiles were removed and the resulting yellow residue taken up in water (10 mL). The pH was increased to 13 by addition of 1N NaOH. Purification via ion-exchange chromotography (AG-1, eluted with acetic acid: 0.2–0.5N) gave the title product in good yield (approx 70–80% depending on H₂O content, Mass Spectrum FAB: MH+ 539.3, MH–Na+561.3). ¹H and ¹³C NMR indicate a high level of purity, i.e negligible amounts of tert butyl functional groups.

d) Preparation of Gd-DO3A-(p-nitrobenzyl)amide 0.5 g of the tris carboxymethyl compound of Example 2(c) was dissolved in H₂O (30 mL). Gd(acetate)₃.4H₂O (approx. 85 molar %, 297 mg) dissolved in H₂O (15 mL) was then added. The initial pH of 3 was adjusted to pH 5–6 by incremental addition of 1N NaOH. The reaction mixture was heated to 77° C. for 24 hours. The reaction was taken to dryness and the residue was redissolved in H₂O (10 mL). A Xylenol orange test was negative. The solution was treated with NaOH until pH 9 was obtained. Water was removed, and the pale yellow residue taken up in methanol (25 mL). Any excess gadolinium was removed via filtration as insoluble Gd(OH)₃. The title product was isolated as a pale yellow solid (840 mg) after removal of volatiles and was characterised by IR and UV-vis spectroscopy. When redissolved in water, a Xylenol orange test was found to be negative.

e) Preparation of Gd-DO3A-(p-aminobenzyl)amide

In a glass bomb reaction vessel Gd-DO3A-(p-aminobenzyl)amide (Example 2(d), 730 mg) was dissolved in water (50 mL). A stir bar and 10% Pd/C (270 mg) were added and the black slurry pressurized with hydrogen (50 psi). After stirring for three days, the solution was filtered and the resulting solution taken to dryness. The title product was isolated as a tan solid (680 mg, 98%). The product was characterised by mass spectrometry, IR and UV-vis spectroscopy.

f) Preparation of Gd-DO3A-(P-isothiocyanatebenzyl)amide

Under nitrogen, Gd-DO3A-(p-aminobenzyl)amide (Example 2(e), 680 mg) was dissolved in deoxygenated H₂O (10 mL) and thiophosgene (Cl₂C=S) (one molar equiv, 72 μL) was added to CHCl₃ (8 mL) in a separate flask. The thiophosgene solution was added completely and rapidly to the aqueous solution and the mixture stirred under N₂ for 18 hours. The crude product was chased with H₂O (1×30 mL) and the title product was isolated as a light grey solid (620 mg, approx. 90% yield). Characterisation was accomplished with mass spectrometry IR, UV, Karl Fisher (14% H₂O) and Chloride (9% Cl-) analysis. The presence of the compound of Example 2(e) was not detected.

EXAMPLE 3 a) Preparation of phosihazene G₀, {NP(NH₂CH₂C[O]NHCH₂CH₂NH₂)₂}₃

{NP(NH₂CH₂CO₂C₂H₅)₂}₃ (1.6 g, 2.1 mmol) was dissolved in ethanol (50 mL) in a 100 mL Schlenk flask. Freshly distilled ethylenediamine (EPA) (150 mL) and ethanol (40 mL) were placed in a separate Schlenk flask and the resulting solution cooled to 0° C. Both solutions were thoroughly purged with N₂ for 30 minutes with stirring and the following reaction and workup conducted under N₂. The phosphazene solution was then added dropwise via cannula to the cooled EDA solution. After stirring at 0° C. for 3 days, the solution was warmed to 25° C. A small aliquot was removed, the volatiles were taken off and the resulting small amount of oily residue was found to be the title product (¹H and ³¹P NMR spectroscopy). The reaction mixture was similarly worked up and the crude product chased with ethanol/toluene (1:10, 100 mL). The title product was dried in vacuo to give a light yellow solid in high yield. The ³¹P NMR spectrum contained a single resonance at 21.04 ppm (cf starting material, 19.58 ppm).

b) Preparation of phosphazene G₀ poly-Gd-DO3A

In separate flasks are placed the G₀ dendrimer of Example 3(a) and the GdDO3A-NCS of Example 2(f). Deionized water is added to each flask (10 and 40 mL, respectively). The pH values are noted (10.2 and 9.2) and the two solutions are combined. The pH is then adjusted to a value of 8.95. After six days the volatiles are removed and the crude solid is purified on a size exclusion column to give the title product as a pale yellow solid.

EXAMPLE 4 a) Preparation of [O=P(OCH₂CH₂NH₃)₃]³⁺3 Cl—

Into a three-neck flask fitted with a reflux condenser, N₂-adapter, and thermometer, is placed freshly distilled ethanolamine. The solution is cooled and freshly distilled phosphorous oxychloride is added at a rate such that the temperature of the reaction stays below 90° C. The mixture is stirred for 2 hours at which time the product is washed with toluene. The title product crystallizes upon being boiled in absolute ethanol. The free base [O=P(OCH₂CH₂NH₂)₃]

is obtained upon treatment of the HCl salt with freshly generated sodium ethoxide.

b) Preparation of [O=P(OCH$_2$CH$_2$N{CH$_2$CH$_2$CO$_2$Et}$_2$)$_3$]

In a two-neck flask fitted with a N$_2$-adapter, absolute ethanol is added to [O=P(OCH$_2$CH$_2$NH$_2$)$_3$] (Example 4(a)). In a separate flask, freshly distilled ethyl acrylate is dissolved in ethanol and the resulting solution is added to the phosphate ester solution. After stirring for three days, the volatiles are removed in vacuo to give the title product as a viscous, colorless oil.

c) Preparation of phosphate ester cored dendrimer—poly-Gd-D03A

The phosphate ester-cored dendrimer of Example 4(b) is loaded with Gd-D03A chelate moieties analogously to Example 3(b) by reaction with Gd-D03A-NCS.

EXAMPLE 5

DENRIMER CORE HYDROLYSIS a) Phosihazene G$_0$, {NP(NH$_2$CH$_2$C[O]NHCH$_2$CH$_2$NH$_2$)$_2$}$_3$ One of the advantages of the dendrimeric backbone polymers used according to the invention relative to the conventional PAMAM dendrimers is increased susceptibility to hydrolysis. The hydrolysis of phosphazene G$_0$ (the compound of Example 3(a)) in D$_2$O was followed by $^{31}$P NMR spectroscopy. The following Table summarizes the results:

| Run | pH | Reaction Temp. | Time | Degradation | Misc |
|---|---|---|---|---|---|
| 1 | 7.1 | 37° C. | 3 d | None | In the presence of Seronorm ™ |
| 2 | 11.0 | 37° C. | 5 d | None | |
| 3 | 1.2 | 37° C. | 4 d | 85% | |
| 4 | 7.0 | 25° C. | 3 d | 30% | In the presence of semi-purified Rat Liver |

The hydrolysis experiments were conducted in 5 mm NMR tubes. The pH values were measured in the tubes using a narrow bore pH electrode. pH was adjusted using 10% HCl or 40% NaOD. D$_2$O was purchased from Aldrich Chemical Co.. Temperatures were recording using a Hg thermometer and were not corrected.

The results of Run 1 suggested that hydrolysis in the blood is not likely. However, the results from Run 4 indicate that blood pool agents based on such cores, which may have molecular weights in excess of 50 kD and would eventually be taken up by the liver, are liable to break down in the liver.

Chopped rat liver was used as a crude representation of enzymes that blood pool agents might encounter. $^{31}$P NMR spectroscopy clearly showed 30% degradation after 3 days. 20% of the starting phosphazene had degraded within the first three hours of exposure to the contents of the rat liver. Normally, enzyme activity drops off rapidly in vitro after the first few hours of cell lysis due to enzyme cannibalism.

The liver experiment was conducted using freshly blended rat liver which was spun down by centrifugation to separate the solids. The homogenate was then added to a preadjusted (pH=7) solution of phosphazene G$_0$. For comparison, $^{31}$P NMR spectra of pure rat liver (no signal) and starting phosphazene G$_0$ were taken. Only the spectrum of the treated phosphazene G$_0$ contained a new signal (2.5 ppm).

EXAMPLE 6 a) Reaction of $^P$G$_o$ with DO3A-NCS

The reaction was set up in a 5mm NMR tube and reaction progress was monitored by $^{31}$P NMR spectroscopy. Initially, 6.9 equivalents of DO3A-NCS were utilized, enough to provide for complete reaction. However, the NMR spectrum contained at least three discernable resonances. Addition of more DO3A-NCS resulted in a rapid change in these product ratios until finally, a single resonance was present indicating the reaction had proceeded to a single product.

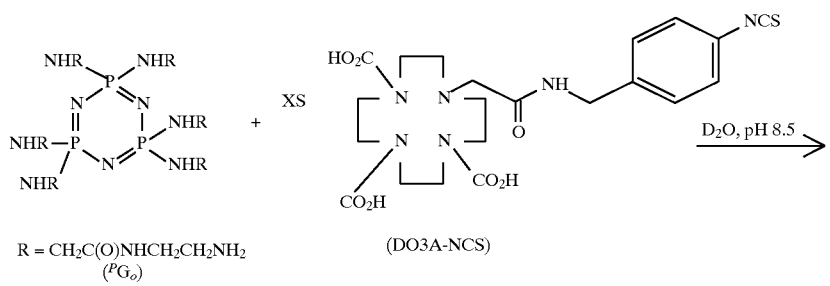

R = CH$_2$C(O)NHCH$_2$CH$_2$NH$_2$
($^P$G$_o$)

(DO3A-NCS)

-continued

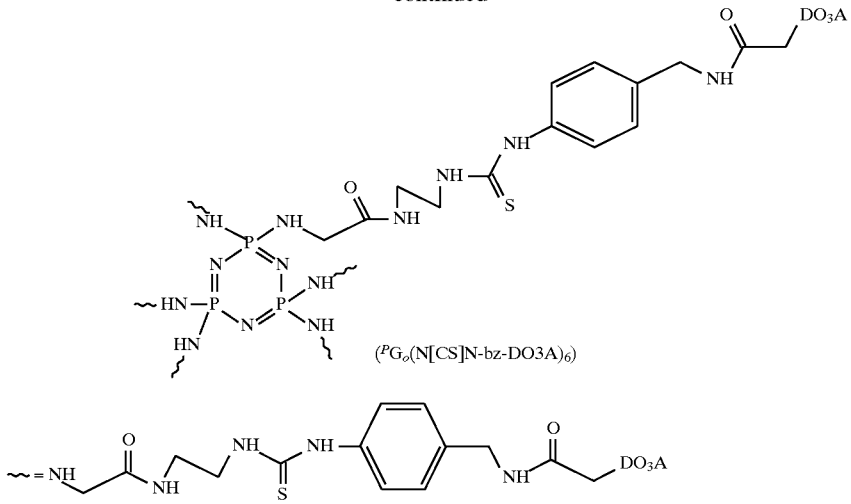

($^PG_o(N[CS]N$-bz-DO3A$)_6$)

∼ = $NH$—C(O)—NH—CH$_2$CH$_2$—NH—C(S)—NH—(C$_6$H$_4$)—CH$_2$—NH—C(O)—CH$_2$—DO$_3$A b) Hydrolysis of $^PG_o(N[CS]N$-bz-DO3A$)_6$ $^PG_o(N[CS]N$-bz-DO3A$)_6$ from Example 6(a) was used.

Three experiments were conducted with the following conditions:

a) Mouse whole blood, D$_2$O (pH 6.5), 37° C.

b) Mouse liver, purified by spinning (some solids), D$_2$O, 37° C.

c) Mouse liver, Tween detergent (to liberate membrane bound enzymes), purified by spinning (some solids), D$_2$O, 37° C.

Each experiment resulted in the formation of a new product characterized as the mono-hydrolyzed species, N$_3$P$_3$(NHR)$_5$(OH). This product results from the selective cleavage of a single arm from the phosphazene core.

The possibility of a product forming by interaction of a unmodified core with a large biomolecule was ruled out since ultrafiltration through a Centriprep C-10 unit resulted in a material with the same spectroscopic properties as seen in the initial experiment. No biomolecules (proteins, enzymes etc.) will pass through the 10,000 MW cutoff filter.

The relative rates of hydrolysis as followed by integrating the $^{31}$P NMR spectra are as follows: Liver with Tween≧Liver>>Whole Blood.

The formation of the initial hydrolysis product N$_3$P$_3$(NHR)$_5$(OH) was expected to be stable at neutral pH but quite unstable at lower pH values.

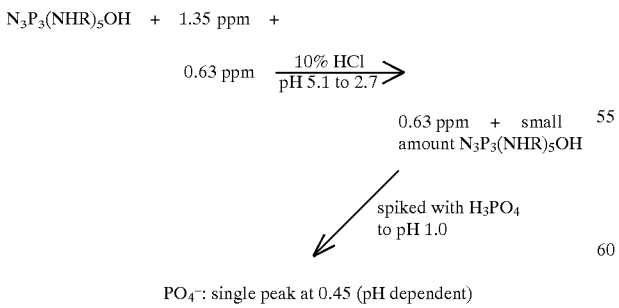

PO$_4^-$: single peak at 0.45 (pH dependent)

This was indeed found to be the case. After combining the contents from the two liver experiments and filtering, the new pH was 5.1 and the ratio of N3P$_3$(NHR)$_5$(OH) to phosphate, was altered to favor phosphate. Further lowering of the pH to 2.7 resulted in near quantitative conversion to phosphate (spiking with H$_3$PO$_4$ resulting in the presence of a single peak in the $^{31}$P NMR spectrum).

EXAMPLE 7

(a) Preparation of Oligolysine

Solid phase peptide synthesis (SPPS) is used to fabricate oligomeric lysine units in a fashion similar to that used to make small branched homo-lysine peptides (see Tam, Proc. Natl. Acad. Sci. USA, 85, 5409, (1988); Denkewalter et al. U.S. Pat. No. 4,289,872; Tam, WO 90/11778).

For production of oligomeric non-branched lysine peptides it is necessary to block the ε-amino of Lys, usually done with tert-butyloxycarbonyl (Boc) introduced by Boc-N$_3$ to copper-complexed Lys (see Schwyzer et al. Helv. Chim. Acta 44:159 (1961)). Techniques for blocking (protecting) and deprotecting amino acids during SPPS are well-developed (see Fields et al., Int. J. Peptide Protein Res. 35, 161, (1990)).

The addition of protected lysine units is repeated until an oligomer (from 5–20 monomers) is achieved at which time the free peptide is cleaved from the solid support using strong acid (HF or TFMSA) or TFA.

(b) Preparation of Chelant-Oligolysine

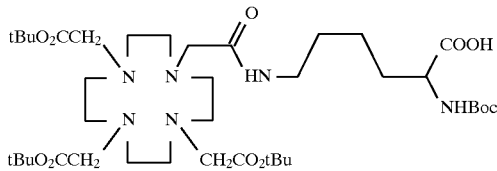

α-Boc-Lys is added to ClCH$_2$COCl in the presence of base to give the ε-amide derivative.

This is then reacted with DO3A.HBr in acetonitrile in the presence of TMG or suitable base to give the t-butyl ester DOTA-Lys derivatised acid. A similar EDTA derivative of lysine has been reported (Rama et al. Tet. Lett. 33:4521 (1992)).

(c) Formation of Chelate-oligolysine Units (i) From the product of Example 7(b)—removal of the t-Bu groups of DOTA is accomplished by standard techniques and is followed by incorporation of Gd (from $Gd_2O_3$). The resulting metal chelate-amino acid is oligomerized using standard (SPPS) techniques.

(ii) oligomerization of the chelate-lysine monomer unit of Example 7(b) s accomplished using SPPS. This is followed by addition to $Gd_2O_3$. The resulting metal-chelate oligolysine unit is cleaved from the solid support by conventional methods.

(iii) From the product of Example 7(a) the tethered oligolysine unit is deprotected in the ε-position and is then reacted with an appropriate DO3A derivative, e.g.

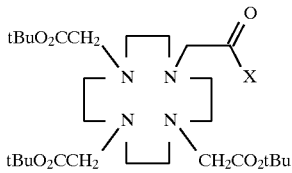

(where X=Cl, Br, OMe etc.) in the presence of base to give the desired chelate-oligolysine unit which is isolated after acidic cleavage from the solid support. This may be followed by incorporation of Gd to give the metal-chelate oligolysine compound.

(d) Attachment of oligolysine unit to dendrimers to form magnifiers

A number of approaches exist to attach lysine units to dendrimers.

a) Either of the end groups (—C(O)OR (n+½ generation) or —$NH_2$ (1, 2, 3, ... nth generation)) are reacted with the N-terminus or C-terminus of oligolysine, respectively, to form a new amide bond i) From the product of Example 7(a), the oligolysine unit is reacted with dendrimer in an appropriate solvent (e.g. MeOH, $H_2O$) to give an oligolysine-dendrimer conjugate. The ε-amine groups are deprotected and then reacted with functionalized DO3A to attach the chelate to the peptide chains. This is followed by treatment with $Gd_2O_3$ thus incorporating Gd into the chelate and forming the magnifier.

ii) From Example 7(c)(iii), an analogous reaction is employed but starting with the metal-chelate oligolysine unit.

b) Linker molecules are utilized for attaching peptide chains to the dendrimer thus imparting controlled biodegradable behaviour. For example, this may proceed via attachment of amino acids as linkers (alanine, glycine etc.) by known methods (see, for example, Clegg et al. Bioconjugate Chem., 1:425, (1990)) to either the dendrimer end groups or previously to oligolysine unit allows retention time in blood pool to be controlled and allows characterization of metabolic products.

Numerous other linker molecules are employable (see Means et al. Bioconjugate Chem. 1:2 (1990); and Brinkley, Bioconjugate Chem. 3:2 (1992)).

EXAMPLE 8

Preparation of PEG-modified Generation 4 dendrimer loaded with Gd macrocycles: $\{G_4(N[CS]N\text{-}bz\text{-}DO3A)_{30}\}$ (i) Preparation of Generation 4 Dendrimer The same procedure was followed as in Watson (WO93/06868) to generate a Generation 4.0 dendrimer. $G_4$ (0.56 g) was dissolved in d.i. $H_2O$ (20 mL) and in a separate flask, DO3A-bz-NCS (i.e.

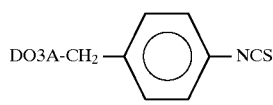

(2.31 g, 20% excess) was dissolved in $H_2O$ (80 mL) and the pH adjusted with 5N NaOH to 8.5. The latter solution was slowly added (small aliquots) to the dendrimeric solution with vigorous stirring. The addition was complete within 10 min. After stirring for four days, the solution was passed through a medium porosity frit and the volatiles removed by roto-evaporation (heat setting 60). 0.48 g of the light orange solid was taken and filtered using Centriprep C-10 filter. This was shown by GPC to effectively separate the low molecular weight impurities from the desired product. The rest of the crude mixture was filtered in this manner and a total of 2.1 g of product was isolated. Integration of the $^1H$ NMR spectrum gave an approximate average loading of 30 chelates per dendrimer (y=30) for a 63% loading efficiency. The product was also characterized by $^{13}C$ NMR and CZE analysis.

(ii) Gadolinium Incorporation: The product of Example 8(i) (551 mg) was dissolved in d.i. $H_2O$ (11 mL) while $Gd(OAc)_3 \cdot 4H_2O$ (0.90 g) was dissolved in 8 mL of $H_2O$. The dendrimer solution was added to the latter since not all of the gadolinium acetate had solubilized. Additional $H_2O$ was added (10 mL) and the pH checked (5.0). After 24 h at ambient temperature, the solution was heated to 45° C. for 3.5 h. The resulting solution was filtered (2×45 min) using Centreprep C-10 filters to remove most of the unreacted gadolinium salts. The pH of the resulting solution was raised to 9 to precipitate any unreacted gadolinium as $Gd(OH)_3$ and filtered through a 0.45μ filter. A Xylenol Orange test was negative for free gadolinium. Removal of chloride salts was by ultrafiltration, and was monitored by GPC. This resulted in the formation of a pure product (≈300 mg).

(iii) Reaction of PEG-SPA with $\{G_4(N[CS]N\text{-}bz\text{-}DO3A\text{-}Gd)_{30}\}$ The product of Example 8(ii), $G_4(N[CS]N\text{-}bz\text{-}DO3A\text{-}Gd)_{30}$ (160 mg, $5.3\times10^{-6}$ mol), and PEG-SPA 5000 (480 mg, $9.6\times10^{-5}$ mol, Shearwater Chemical were placed in separate flasks to which deionized water was added (10 mL, respectively). The slightly cloudy PEG solution was added rapidly to $G_4(N[CS]N\text{-}bz\text{-}DO3A\text{-}Gd)_{30}$ and the resulting solution (pH 7.8) was stirred at ambient temperature for 24 h. The solution was purified using ultrafiltration (Centriprep C-10 and C-30). TLC (MeOH/$CHCl_3$, 1:1) showed removal of PEG species to be efficient. The product was characterized by conventional spectroscopic methods (NMR, IR, UV) and light scattering (LALLS, PCS).

We claim:

1. A dendrimeric compound or a salt thereof, said compound comprising a biodegradable core moiety and a dendrimeric backbone moiety, wherein said core moiety is a phosphazene or a boron-based core of the formula:

in which X is carbon, oxygen, or nitrogen, each X, independently, is unsubstituted or substituted with R or $[Y'-X']_q$; Y is boron or phosphorus, each Y, independently, is unsubstituted or substituted with R or $[X'-Y']_q$; X' and Y' are as defined for X and Y, respectively, but cannot carry side chains $[Y'-X']_q$ or $[X'-Y']_q$; each R, independently, is hydrogen, oxo, or a bond; and q is 2–5; and two non-adjacent Y groups can together represent a single Y group thereby, together with the intervening X and Y groups, creating a 4 to 10 membered ring; and said backbone moiety has linked thereto a plurality of diagnostically or therapeutically active moieties, characterised in that the molecular skeleton of said compound contains at least one biodegradable cleavage site such that on cleavage thereof said active moieties are released in renally excretable form.

2. A compound as claimed in claim 1 wherein said active moieties comprise chelant moieties.

3. A compound as claimed in claim 2 wherein said active moieties comprise chelant moieties metallated with diagnostically or therapeutically effective metal ions.

4. A compound as claimed in claim 3 wherein said metal ions are selected from paramagnetic metal ions, heavy metal ions and ions of radionuclides.

5. A compound as claimed in claim 1 wherein said dendrimeric backbone is an up to eighth generation dendrimer.

6. A compound as claimed in claim 1 wherein said cleavage site of the backbone moiety is at a dendrimeric branching site.

7. A compound as claimed in claim 6 wherein said cleavage site comprises a polyatomic structure containing at least one atom other than carbon in its backbone.

8. A compound as claimed in claim 1 having at least one said cleavage site outside said dendrimeric backbone.

9. A compound as claimed in claim 1 which on biodegradation releases uniform renally excretable biodegradation products.

10. A compound as claimed in claim 1 further comprising at least one biodistribution modifying moiety attached to said molecular skeleton so as to enhance solubility of said compound, prolong the blood residence time of said compound, or direct said compound to desired tissue or body sites.

11. A compound as claimed in claim 10 wherein said biodistribution modifying moiety is tissue or body site-directing groups, which are molecules that naturally concentrate in a selected target organ, tissue, cell, or group of cells, or other location in a mammalian body, being selected from the group consisting of amino acids, oligopeptides, molecular recognition units, single chain antibodies, antibodies or fragments thereof, polysaccharides, collagen, bile acids, lipids and derivatives thereof, wheat germ agglutinin, complement components, complement component fragments, cytokines, eicosanoids, fibronectin, ferritin, transferrin, hemoglobin, epidermal growth factor, mannose-6-phosphate, ligands, lectins, asialofetuin, polyclonal immunoglobulin G, blood clotting proteins, lipoproteins, glycoproteins, hormones, growth factors, nucleic acids, deoxyribonucleic acids, antigens, haptens, clotting factors, polymerized fibrin fragments, serum amyloid precursor proteins, low density lipoprotein precursors, serum albumin, surface proteins of intact red blood cells, estrogens, galactosyl-neoglycoalbumin, N-(2-hydroxy-propyl) methacrylamide copolymers with bound galactosamines, allyl and 6-aminohexyl glycosides, fibrinogen, and a site-specific peptide, hydrophilic groups, lipophilic groups, and protein-binding inhibiting groups.

12. A compound as claimed in claim 11 wherein said biodistribution modifying moiety is a polyalkyleneoxide, modified polyethylene glycol, peptide or carbohydrate.

13. A compound as claimed in claim 1 having a molecular weight in the range $10^3$ to $10^5$ Daltons.

14. A process for the preparation of a compound as claimed in claim 1, said process comprising (i) conjugating a plurality of diagnostically or theraputically active moieties to a dendrimer; or (ii) metallating chelant moieties linked to a dendrimeric backbone moiety with therapeutically or diagnostically effective metal ions.

15. A diagnostic or therapeutic composition comprising a dendrimeric compound as claimed in claim 1, or a salt thereof, together with at least one pharmaceutical carrier or excipient.

16. A method of generating an image of a human or non-human animal body which method comprises administering to said body an image enhancing amount of a dendrimeric compound as claimed in claim 1 or a salt thereof and thereafter generating an image of at least a part of said body.

17. A method of therapy of the human or animal body said method comprising administering to said body a therapeutically effective amount of a dendrimeric compound as claimed in claim 1.

* * * * *